US009149309B2

(12) United States Patent
Paczkowski et al.

(10) Patent No.: US 9,149,309 B2
(45) Date of Patent: Oct. 6, 2015

(54) SYSTEMS AND METHODS FOR SKETCHING DESIGNS IN CONTEXT

(75) Inventors: Patrick Paczkowski, New Haven, CT (US); Julie Dorsey, Madison, CT (US); Min Hyuk Kim, Daejeon Chungnam (KR); Holly Rushmeier, Old Saybrook, CT (US)

(73) Assignee: Yale University, New Haven, CT (US)

( * ) Notice: Subject to any disclaimer, the term of this patent is extended or adjusted under 35 U.S.C. 154(b) by 165 days.

(21) Appl. No.: 13/551,879

(22) Filed: Jul. 18, 2012

(65) Prior Publication Data
US 2013/0223691 A1 Aug. 29, 2013

Related U.S. Application Data

(60) Provisional application No. 61/604,909, filed on Feb. 29, 2012.

(51) Int. Cl.
*A61B 17/80* (2006.01)
*G06K 9/00* (2006.01)

(52) U.S. Cl.
CPC .............. *A61B 17/80* (2013.01); *A61B 17/8033* (2013.01); *G06K 9/00671* (2013.01)

(58) Field of Classification Search
USPC ........................................................ 382/106
See application file for complete search history.

(56) References Cited

U.S. PATENT DOCUMENTS

| 2003/0164838 A1 | 9/2003 | Guo et al. |
| 2005/0007378 A1 | 1/2005 | Grove |
| 2005/0128210 A1 | 6/2005 | Berger |
| 2006/0020204 A1 | 1/2006 | Serra et al. |
| 2006/0082571 A1 | 4/2006 | McDaniel |
| 2006/0232583 A1 | 10/2006 | Petrov et al. |
| 2007/0122027 A1 | 5/2007 | Kunita et al. |
| 2007/0146360 A1 | 6/2007 | Clatworthy et al. |
| 2007/0146372 A1 | 6/2007 | Gee et al. |
| 2007/0182738 A1 | 8/2007 | Feldman et al. |
| 2008/0001962 A1 | 1/2008 | Lefebvre et al. |
| 2008/0252527 A1 | 10/2008 | Garcia |

(Continued)

OTHER PUBLICATIONS

Bae, S.H., et al., "ILoveSketch: As-Natural-As-Possible Sketching System for Creating 3D Curve Models", Proceedings of the 21st Annual ACM Symposium on User Interface Software and Technology (UIST '08), pp. 151-160 (2008).

(Continued)

*Primary Examiner* — Amir Alavi
*Assistant Examiner* — Kenny Cese
(74) *Attorney, Agent, or Firm* — Mintz Levin Cohn Ferris Glovsky and Popeo, P.C.

(57) ABSTRACT

A method, a system, and a computer program product for graphically representing physical objects in a contextual setting are disclosed. A first data for a predetermined location, at least one distance measurement between at least two location points at the predetermined location, and at least one image of at least one portion of the predetermined location can be received. Based on the receiving and information obtained from at least one publicly available resource, a spatial representation of the predetermined location configured to include at least one existing feature can be generated. Spatial representation of the predetermined location includes a detailed representation of the at least one portion of the predetermined location having the at least one existing feature.

33 Claims, 19 Drawing Sheets
(17 of 19 Drawing Sheet(s) Filed in Color)

(56) References Cited

U.S. PATENT DOCUMENTS

| | | | |
|---|---|---|---|
| 2009/0284550 A1 | 11/2009 | Shimada et al. | |
| 2009/0315978 A1 | 12/2009 | Wurmlin et al. | |
| 2010/0007669 A1* | 1/2010 | Bethune et al. | 345/520 |
| 2010/0085351 A1 | 4/2010 | Deb et al. | |
| 2010/0141648 A1 | 6/2010 | Bell et al. | |
| 2010/0225642 A1 | 9/2010 | Murray et al. | |
| 2010/0293193 A1* | 11/2010 | Harrison et al. | 707/769 |
| 2011/0074772 A1 | 3/2011 | Wada et al. | |
| 2011/0169829 A1 | 7/2011 | Berger et al. | |
| 2011/0176179 A1 | 7/2011 | Judelson | |
| 2011/0202856 A1 | 8/2011 | Handley et al. | |
| 2012/0007862 A1 | 1/2012 | Shefi | |
| 2012/0176366 A1 | 7/2012 | Genova | |
| 2013/0093768 A1 | 4/2013 | Lockerman | |
| 2013/0300740 A1* | 11/2013 | Snyder et al. | 345/420 |

OTHER PUBLICATIONS

Cohen, J.M., et al., "Harold: A World Made of Drawings", Proc. of the symposium on Nonphotorealistic Animation and Rendering (NPAR), pp. 83-90 (2000).

Efros, A.A., et al., "Image Quilting for Texture Synthesis and Transfer", Proceedings of the 28th Annnual Conference on Computer Graphics and Interactive Techniques, SIGGRAPH '01, ACM, pp. 341-346 (2001).

Garland, M., et al., "Parallel Computing Experiences with CUDA", Micro, IEEE 28:4, pp. 13-27, (2008).

Igarashi, T., et al., "Teddy: A Sketching Interface for 3D Freeform Design", SIGGRAPH '99, pp. 409-416 (1999).

Kallio, K., "3D6B Editor: Projective 3D Sketching with Line-Based Rendering", Proc. of Eurographics Workshop on Sketch-based Interfaces and Modeling, pp. 73-79 (2005).

Kalnins, R.D., et al., "WYSIWYG NPR: Drawing Strokes Directly on 3D Models", ACM Trans. On Graph. 21:3, pp. 755-762 (2002).

Lau, M., et al., "Modeling-In-Context: User Design of Complementary Objects with a Single Photo", Proc. Symposium on Sketch-Based Interfaces and Modeling, pp. 1-8 (2010).

Muja, M., Flann, Fast Library for Approximate Nearest Neighbors (2009).

Olsen, D.R., Jr., et al., "Edge-Respecting Brushes", Proceedings of the 21st Annual ACM Symposium on User Interface Software and Technology (UIST '08), ACM, pp. 171-180 (2008).

Pollefeys, M., et al., "Visual Modeling with a Hand-Held Camera", Int. J. Computer Vision, 59:3, pp. 207-232 (2004).

Rother, C., et al., "Grabcut: Interactive Foreground Extracting Using Interated Graph Cuts", ACM Trans. Graph. 23, pp. 309-314 (2004).

Sachs, E., et al., "3-Draw: A Tool for Designing 3D Shapes", IEEE Comput. Graph. Appl., 11:6, pp. 18-26 (1991).

Sando, T., et al., "Effects of Animation, User-Controlled Interactions, and Multiple Static Views in Understanding 3D Structures", Proc. Applied Perception in Graphics and Visualization, ACM, pp. 69-76 (2009).

Snavely, N., "Phototourism: Exploring Photo Collections in 3D", ACM Trans. Graph 25:3, pp. 835-846 (2006).

Sollenberger, R.L., et al., "Effects of Stereoscopic and Rotational Displays in a Three-Dimensional Pathtracing Task", Human Factors 35:3, pp. 483-499 (1993).

Sutherland, I.E., et al.., "Sketchpad: A Man-Machine Graphical Communication System", New York Garland Publishers (1980).

Tolba, O., et al.., "A Projective Drawing System", Proc. of Symposium on Interactive 3D graphics (513D), pp. 25-34 (2001).

Tsang, S., et al., "A Suggestive Interface for Image Guided 3D Sketching", Proc. Of the SIGCHI Conference on Human Factors in Computing Systems (CHI), pp. 591-598 (2004).

Ventura, J., et al., "A Sketch-Based Interface for Photo Pop-Up", Proc. Eurographics Symposium on Sketch-Based Interfaces and Modeling, pp. 21-28 (2009).

Zeleznik, R.C., et al.., "Sketch: An Interface for Sketching 3D Scenes", SIGGRAPH '96, pp. 163-170 (1996).

International Search Report for PCT/US2012/059742 mailed Mar. 11, 2013.

International Search Report for PCT/US2013/050707 mailed Jan. 15, 2014.

* cited by examiner

SYSTEMS AND METHODS FOR SKETCHING DESIGNS IN CONTEXT

CROSS-REFERENCE TO RELATED APPLICATIONS

The present application claims priority to U.S. Provisional Patent Application No. 61/604,909 to Dorsey et al., filed Feb. 29, 2012, and entitled "Insitu: Sketching Architectural Designs in Context," and incorporates its disclosure herein by reference in its entirety.

GOVERNMENT RIGHTS

This invention was made with government support under 1044030 and 1018470 awarded by National Science Foundation. The government has certain rights in the invention.

TECHNICAL FIELD

The subject matter described herein relates to data processing and in particular, to methods and apparatus that can implement use of various techniques in computer graphics for integrating various types of data (e.g., photographic, geographic, coordinates, etc.) into a configuration representative of physical object(s) and/or abstractions of such physical object(s) in their physical context.

BACKGROUND

Graphics are visual presentations on some surface, such as a wall, canvas, computer screen, paper, or stone to brand, inform, illustrate, or entertain. Examples of graphics include photographs, drawings, line art, graphs, diagrams, typography, numbers, symbols, geometric designs, maps, engineering drawings, or other images. Graphics can combine text, illustration, and color. Graphic design can include deliberate selection, creation, or arrangement of typography alone, as in a brochure, flier, poster, web site, or book without any other element.

Computer graphics sometimes can refer to representation and manipulation of image data by a computer, various technologies that can be used to create and manipulate images, images that are produced, digital synthesizing and manipulating of visual content, and/or many other things. Computers and computer-generated images touch many aspects of daily life. Computer imagery is found on television, in newspapers, in weather reports, in medical investigation and surgical procedures, as well as many other areas. Many powerful tools have been developed to visualize data. Computer generated imagery can be categorized into several different types: 2D, 3D, and animated graphics. As technology has improved, 3D computer graphics have become more common, but 2D computer graphics are still widely used. Computer graphics has emerged as a sub-field of computer science which studies methods for digitally synthesizing and manipulating visual content. Over the past decade, other specialized fields have been developed (e.g., information visualization, scientific visualization, etc.) that are more concerned with the visualization of three dimensional phenomena (e.g., architectural, meteorological, medical, biological, etc.), where the emphasis is on realistic renderings of volumes, surfaces, illumination sources, and the like, sometimes with a dynamic (time) component.

Computer graphics typically include various visual textures. A texture can refer to a perceived surface quality of an image or an object displayed in an image and can be an element of two-dimensional and three-dimensional design. It can be distinguished by its perceived visual and physical properties. In computer graphics, a texture, such as a bitmap or a raster image, can refer to a detail or a surface texture, or color in a computer-generated graphic or 3D model. An ability to model such visual texture is important in any computer graphics modeling system. The advent of digital photography has made natural images an important source for textures. Numerous texture synthesis techniques have been developed to generate arbitrarily large textures to be mapped onto digital models.

Computer-aided design (CAD) systems have been extraordinarily successful in design, especially in architecture. Recently there has been considerable interest in 3D modeling systems for early phases in the design of structures. Sketching programs that allow users to sketch by hand or "rough out" three-dimensional definitions from simple strokes and gestures are widely used by architects. Yet even as computers are ubiquitous in the design of a physical environment or structures, the existing array of computational aids does not offer assistance in the conceptual design of physical structures relative to existing natural and manmade environments, which can be a central concern of architectural design.

Currently available approaches for representing the surrounding visual context include 3D models and panoramic images. Full 3D models of sites allow a designer to envision designs in multiple views and relative to the context. However, such models are rarely, if ever, used in practice because full-3D models, particularly of landscapes, are difficult to acquire, and the representation is too unwieldy to support conceptual design. Design sketching over photographic panoramas, either on paper or by computer, is often used due to the intuitive interface. However, these sketches cannot easily be reconciled into a 3D form, and testing the compatibility of locations in the site is challenging, if not impossible. Moreover, this approach is very inadequate when complex topographic variations are involved, and sketching on a photograph does not allow for occlusions or multiple views. At best, it can only support the juxtaposition approach, described above—and only for a single view.

A system to support designing relative to context needs to be able to incorporate constraints and features imposed by the existing setting, while allowing free creative experimentation. The key impediment to designing relative to context is the inability to present a complex setting in a form that is amenable to conceptual design. Thus, conventional techniques have not been able to succeed in site representation, design, and imagery.

SUMMARY

In some implementations, the current subject matter relates to a method for sketching of designs in a contextual setting, such as a virtual environment that can be created using a computer based on various input data (e.g., photographs, physical measurements, global positioning system data, etc.), where the virtual environment can correspond to a physical environment in which the architectural design can be implemented as a physical object in the physical environment. The method can include receiving a first data for a predetermined location (for example, but not limited to, geographic data, exterior measurement data, GPS data, interior measurement data (such as measurements for interiors of buildings, rooms, etc.), and/or any other data), at least one distance measurement between at least two location points at the predetermined location, and at least one image of at least one portion of the predetermined location and generating, based on the receiving and information obtained from at least one publicly available resource, a spatial representation of the predetermined location configured to include at least one existing feature can be generated. The spatial representation of the predetermined location can include a detailed representation of the at least one portion of the predetermined location having the at least one existing feature. At least one of the receiving and the generating can be performed using at least one processor.

In some implementations, the current subject matter can include at least one or more of the following optional features. At least one image of the at least one portion can be obtained using an image capturing device disposed at least one location point at the predetermined location. The first data for the predetermined location can include a geographic elevation data.

The generating can include merging the first data for the predetermined location, the at least one distance measurement between at least two location points at the predetermined location, and the at least one image of the at least one portion of the predetermined location and generating at least one user interface for allowing a user to edit the merged first data for the predetermined location, the at least one distance measurement between at least two location points at the predetermined location, and the at least one image of the at least one portion of the predetermined location.

The generated spatial representation of the predetermined location can include a lightweight representation of an environment at the predetermined location.

The spatial representation of the predetermined location can be a three-dimensional representation of the predetermined location.

The method can also include generating at least one new feature based on the at least one existing feature contained within the spatial representation of the predetermined location.

At least one location point at the predetermined location can be configured to define a relative positioning of at least one image of at least one portion at the predetermined location.

In some implementations, the method further includes obtaining at least one additional image of the at least one portion of the predetermined location, merging the first data for the predetermined location, the at least one distance measurement between at least two location points at the predetermined location, the at least one image of the at least one portion of the predetermined location, and the at least one additional image of the at least one portion of the predetermined location, and generating at least one user interface for allowing a user to edit the merged first data for the predetermined location, the at least one distance measurement between at least two location points at the predetermined location, the at least one image of the at least one portion of the predetermined location, and the at least one additional image of the at least one portion of the predetermined location. The method can also include adding at least one drawing stroke to the merged first data for the predetermined location, the at least one distance measurement between at least two location points at the predetermined location, the at least one image of the at least one portion of the predetermined location, and the at least one additional image of the at least one portion of the predetermined location.

In some implementations, the method can also include correcting received first data using the at least one distance measurement between at least two location points at the predetermined location.

Articles are also described that comprise a tangibly embodied machine-readable medium embodying instructions that, when performed, cause one or more machines (e.g., computers, etc.) to result in operations described herein. Similarly, computer systems are also described that can include a processor and a memory coupled to the processor. The memory can include one or more programs that cause the processor to perform one or more of the operations described herein. Additionally, computer systems may include additional specialized processing units that are able to apply a single instruction to multiple data points in parallel. Such units include but are not limited to so-called "Graphics Processing Units (GPU)."

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
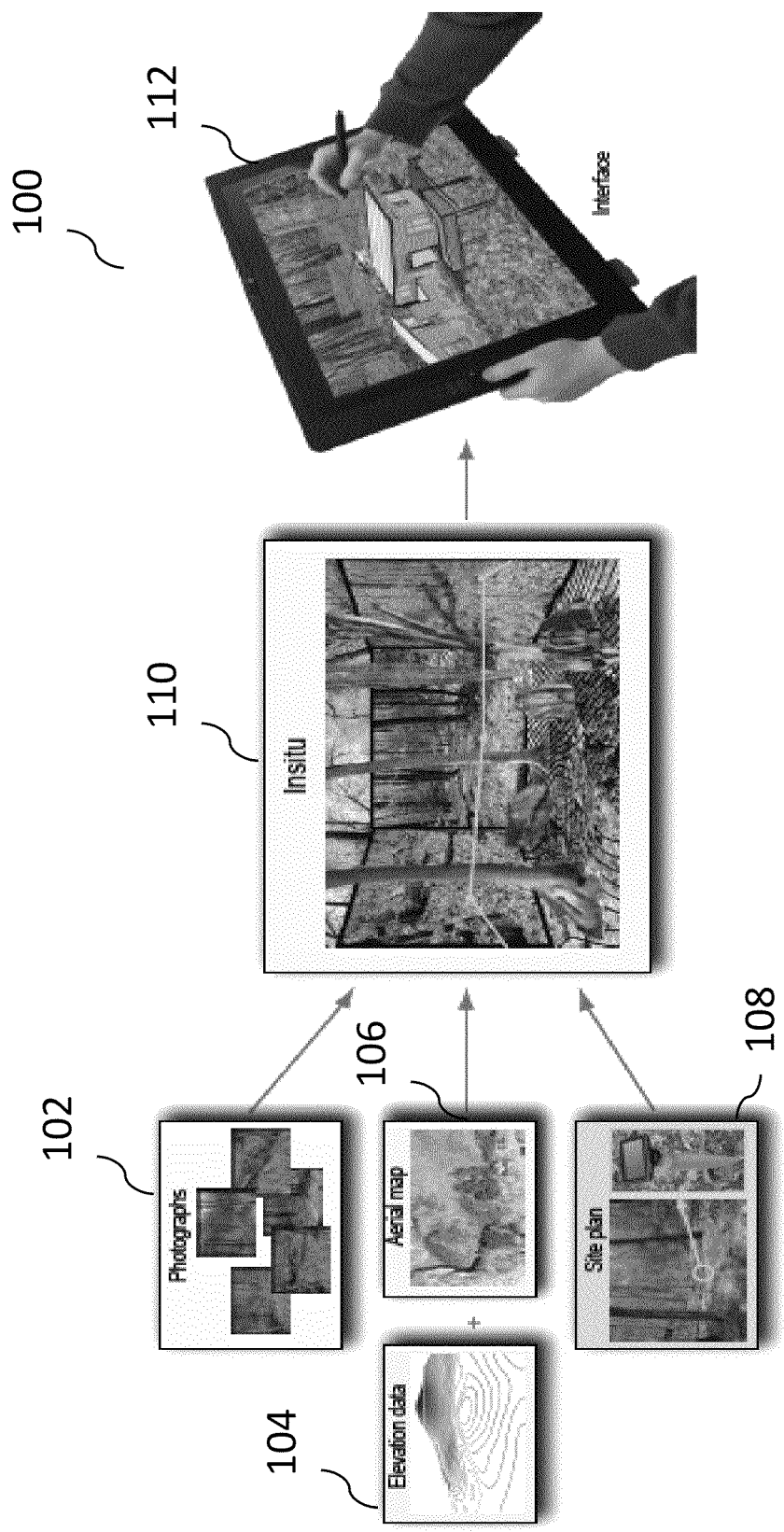
FIG. 1 illustrates an exemplary sketching system, according to some implementations of the current subject matter.

To address the deficiencies of currently available solutions, one or more implementations of the current subject matter provide systems, methods, and computer program products for sketching of various designs in a contextual setting, such as a virtual environment that can be created using a computer based on various input data (e.g., photographs, physical measurements, global positioning system data, etc.), where the virtual environment can correspond to a physical environment in which the design can be implemented as a physical object in the physical environment. In some implementations, the current subject matter can be implemented for sketching architectural designs, various objects, shapes, forms, backdrops, geometrical figures, movie sets, landscape designs, computer games, exterior features, objects, buildings, etc., interior features, objects, rooms, spaces, etc., as well as any other objects, spaces, features, elements, etc., and/or any combination of objects, spaces, features, elements, etc. For ease of discussion and illustrative purposes only, the following discussion may refer to sketching of architectural designs in context, however, it should be understood by one having ordinary skill in the art that concepts discussed in the present application can be applicable to any of the above and other fields.

In some implementations, the current subject matter can use various data that can be obtained from at least one source. Such data can include, but is not limited to a first data for a location, at least one distance measurement between at least two location points at the location, at least one image of at least one portion of the location, as well as any other data. The location can include a physical location or environment, which the user can select for placement of the physical object that the user is attempting to design (e.g., a house (object) in the woods (physical environment)). The first data can include for example, but not limited to, a geographic data (e.g., GPS measurement coordinates), exterior and/or outdoor measurement data (e.g., size, height, width, length, depth, shape, form, relative positioning to at least one object(s) (interior and/or exterior), longitude, latitude, etc. of an exterior of an object (e.g., a building, a house, etc.), an interior and/or indoor measurement data (e.g., size, height, width, length, depth, shape, form, relative positioning to at least one object(s) (interior and/or exterior), longitude, latitude, etc. of an interior of an object (e.g., a room, a space, etc. within a building, a house, etc.)). For illustrative purposes only, the following discussion will refer to geographic data as being obtained for a location, however, it should be understood that such data can be any data discussed above and the present disclosure is not limited to the geographic data or any other specific data that may be discussed herein. The above information can be obtained from any publicly or privately available sources. Some public sources can include, but are not limited to, the United States Geological Service, various municipal departments of towns, cities, etc., geological societies, geographic societies, etc. Some private sources can include, but are not limited to, private land survey companies, insurance companies, etc. The sources can also include global positioning system companies (e.g., Garmin, Ltd. in Olathe, Kans., USA, TomTom International BV in Amsterdam, The Netherlands, etc.), internet companies, (e.g., Google (www.google.com), Yahoo, (www.yahoo.com), etc.)), as well as any other sources. Once the information about the location is obtained, the current subject matter's system can be configured to generate a spatial representation of the location configured to include at least one existing feature, where the feature can be a physical object in the location (e.g., a tree, a rock, etc.). Spatial representation of the location can include a detailed representation of at least one portion of the location having at least one existing feature.

In some implementations, the current subject matter relates to methods and systems for presentation of spatial context, such as, for example, but not limited to, an architectural design, such that it is an integral component in a lightweight conceptual design system. In some implementations, lightweight can refer to the following two aspects: first, the simplicity of the visual representation of both the recreated context and sketched design and resemblance of a simple collection of paper sketches composed with a few photographs; and second, the simplicity of the internal modeling complexity of the context and design. In some implementations, the lightweight characteristics of the current subject matter system can minimize the number of polygons, textures, and/or any other features that are used to create graphical representations of physical objects in the system, without sacrificing any content. The current subject matter can represent physical sites through a fusion of data available from at least one source. For example, a site model can be derived from geographic elevation data, on-site point-to-point distance measurements, images of the site, as well as any other sources, according to some implementations of the current subject matter. To acquire and process the data, publicly available data sources, multi-dimensional scaling techniques and refinements of recent bundle adjustment techniques can be used. In some implementations, a bundle adjustment technique can take a collection of images depicting a 3D scene from different viewpoints, and, through optimization techniques, can resolve: (1) finding the relative parameters of the camera used to acquire each image (e.g., focal length, position, orientation, etc.), and (2) retrieving and/or refining 3D coordinates describing the scene geometry. The current subject matter can provide interactive tools to acquire, process, and combine data into a lightweight stroke and image-billboard representation. Multiple and linked pop-ups that are derived from images can be created, thereby forming a lightweight representation of a three-dimensional environment. In some implementations, a pop-up can be a modal window that can ask a user to interact with it before they can return to operating the parent software application that may have generated the pop-up window as a "child" window. The user can also work simultaneously in the pop-up window and the parent software application. Using the current subject matter system, the user can "sketch" and/or enter strokes on an image. Sketching or stroke-entering can include implementing various computer graphics commands that can correspond to certain operations on various parameters, including for example, entering, changing, adjusting, varying, etc. The various parameters can include, but are not limited to, textures, colors, lines, angles, orientation, and/or any other parameters and/or a combination of parameters of a particular object and/or objects displayed in an image and/or portion(s) of an image and/or the entire image. The object can be a graphical or visual representation of a physical object from the physical environment and/or a virtual object that can be created by the user. The operation(s) can be implemented by typing commands in a computer prompt, moving a mouse cursor or otherwise manipulating an image, a portion of an image, an graphical object displayed on an image using various methods including, but not limited to, a joystick, a mouse, a keyboard, etc., using finger(s) (e.g., such as in the case of an iPad, iPod, iPhone, etc. and/or any other touch screen device), and/or using any other methods and/or combination of methods.

The design of architectural structures, for example, poses substantive and unique challenges. The spatial fit between architecture and its context is one of the concerns, as architecture includes exterior and interior space and typically is not designed in a vacuum. There are three basic relationships between physical objects and its surrounding physical environment: contrast, merger, and reciprocity. Contrast can juxtapose architectural physical objects with the natural context—for example, the relationship of New York City's Central Park (object) to the surrounding physical environment (e.g., City of New York). Merger can be the opposite of contrast: an architectural physical object can be designed to appear as a harmonious integral part of the surrounding physical environment. The architectural physical object and the surrounding physical environment can be conceived as one, making it impossible to design independent of the surrounding physical environment, which cannot be addressed by the current CAD systems. Reciprocity can represent a hybrid condition, in which an architectural physical object and its surrounding physical environment reflect one another and enter into a spatial relationship. The current subject matter system can address these issues by providing the user with an ability to design, using a computer interface, various objects (e.g., buildings, sculptures, monuments, parks, etc.) in existing physical environments by using information (e.g., location data, photographic data, geographic data, etc.) about various aspects of such physical environments as well as the objects being designed to account for the basic relationships between architecture and its surrounding physical environment.

Some implementations of the current subject matter relate to a stroke-based sketching system for representing context, including terrain information, built structures, natural features and other aspects. The sketching system can allow a user to enter strokes on two-dimensional ("2D") planes, which can be positioned in a three-dimensional ("3D") space to lay out a design. As shown in FIG. 1, the sketching system 100 can use various inputs such as photographs 102, elevation data 104, aerial map 106, and site plan 108 as inputs to the context representation 110 that can be manipulated on a computing device 112. The photographs 102 can be taken by the user seeking to sketch the site and can include photographs of the site taken at various angles, from various positions, using different lighting, filters, exposure, and others. The elevation data 104 can be obtained from United States Geological Survey ("USGS") various municipal departments of towns, cities, etc., geological societies, geographic societies, private land survey companies, insurance companies, global positioning system ("GPS") companies (e.g., Garmin, Ltd. in Olathe, Kans., USA, TomTom International BV in Amsterdam, The Netherlands, etc.), internet companies, (e.g., Google (www.google.com), Yahoo, (www.yahoo.com), etc.)), as well as any other sources and/or combination of sources. Aerial map 106 can be obtained from various sources, including Bing Maps (http://www.bing.com/maps/), Google Earth (earth.google.com/), as well as any other sources, including, but not limited to those listed above. The site plan 108 can be obtained through a use of physical stakes placed in the ground at the site in combination or otherwise fused with the coordinates corresponding to the stakes, as discussed below. The coordinates can be obtained from any sources, including, but not limited to, GPS data as well as sources listed above. As shown in FIG. 1, the computing device 112 can be an LCD screen tablet. It can also be any computing device, such as a personal computer, a personal digital assistant ("PDA"), a smartphone device, a PC tablet, an iPhone, an iPad, an iPod, and/or any other device that includes a processing device, a memory, and a screen, and/or any combination of the above. The sketching system 100 can allow fusing data from different sources (e.g., geographic elevation data, on-site point-to-point distance measurements, images of the site, etc.) into a common coordinate system for the purposes of representing the site in context or in-situ. The following is a discussion of some exemplary aspects of the system as well as a presentation of various experiments that were conducted using the stroke-based sketching system 100. The user can perform the sketching operations using an interface that is present on the user's computing device 112.

Figure 2:
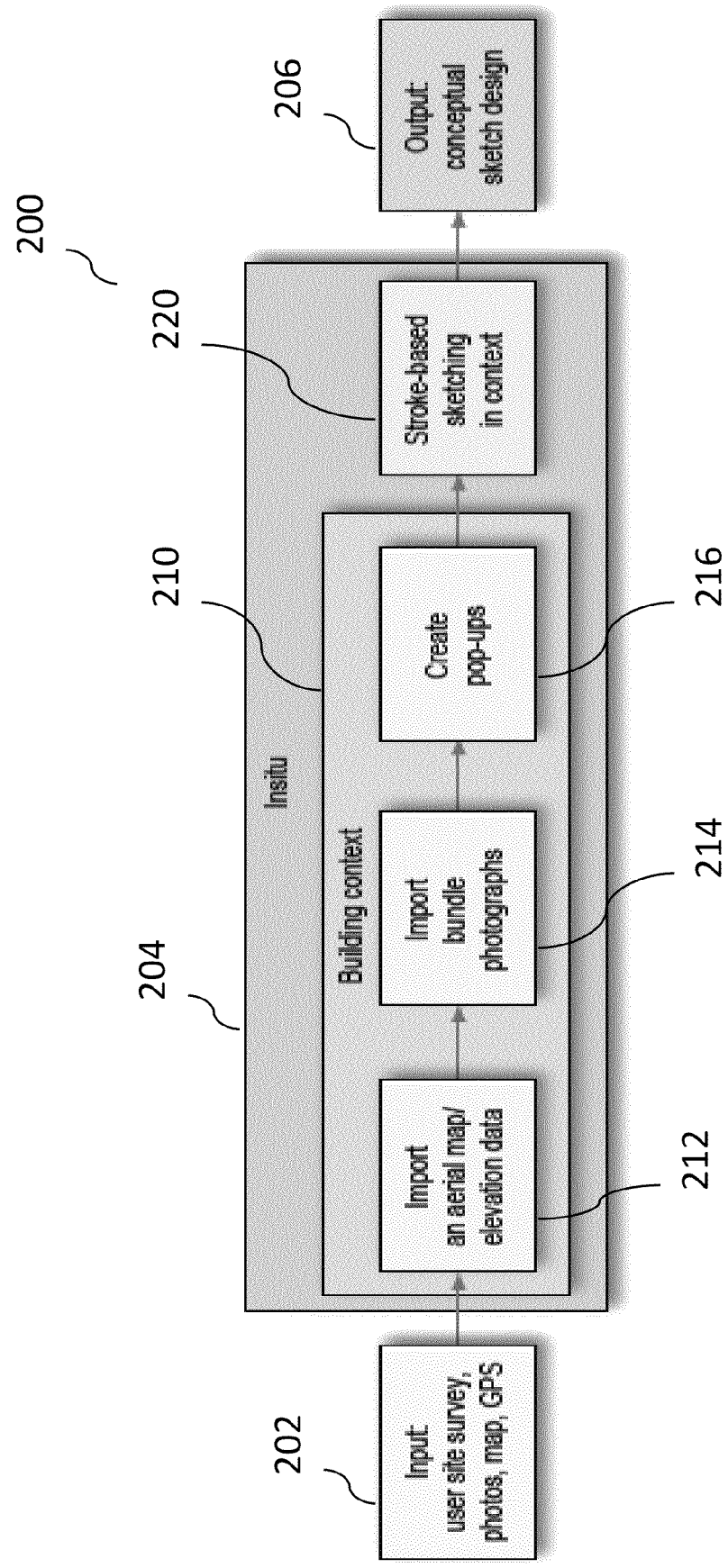
FIG. 2 illustrates an exemplary sketching system methodology, according to some implementations of the current subject matter.

FIG. 2 illustrates an exemplary process 200 for capturing or sketching a site environment to be used as context in a conceptual design, according to some implementations of the current subject matter. At 202, input information can be gathered about the site. Such information can include photographs, an aerial map, coordinates, site survey information, etc. The gathered information can be submitted for stroke-based sketching, at 204. The stroke-based sketching can include building context phase 210 and stroke-based sketching phase in context 220. The building context phase 210 can include importing of an aerial map/elevation data concerning the site sub-phase 212, importing of a bundle of photographs 214, and creating of pop-ups 216. The aerial map/elevation data can be imported into the system to form the base of a virtual site that can represent the real site being captured. Photographs can be bundle-adjusted and imported into the system, which can yield a lightweight representation, consisting of pop-ups positioned in space. This context representation and visualization can be used to guide the development of stroke-based sketching of designs in context and reconciled with the site. An output of the system 200 can include a conceptual sketch design, at 206. In some implementations, the user can manually select a collection of photographs that the use would like to include in the virtual site. This collection can be used as input for the bundle adjustment algorithm, which can yield one or more of bundles of one or more photographs. In some implementations, "bundles" with a single photograph can be photographs that could not be aligned with any other photograph in the collection.

Figure 3:
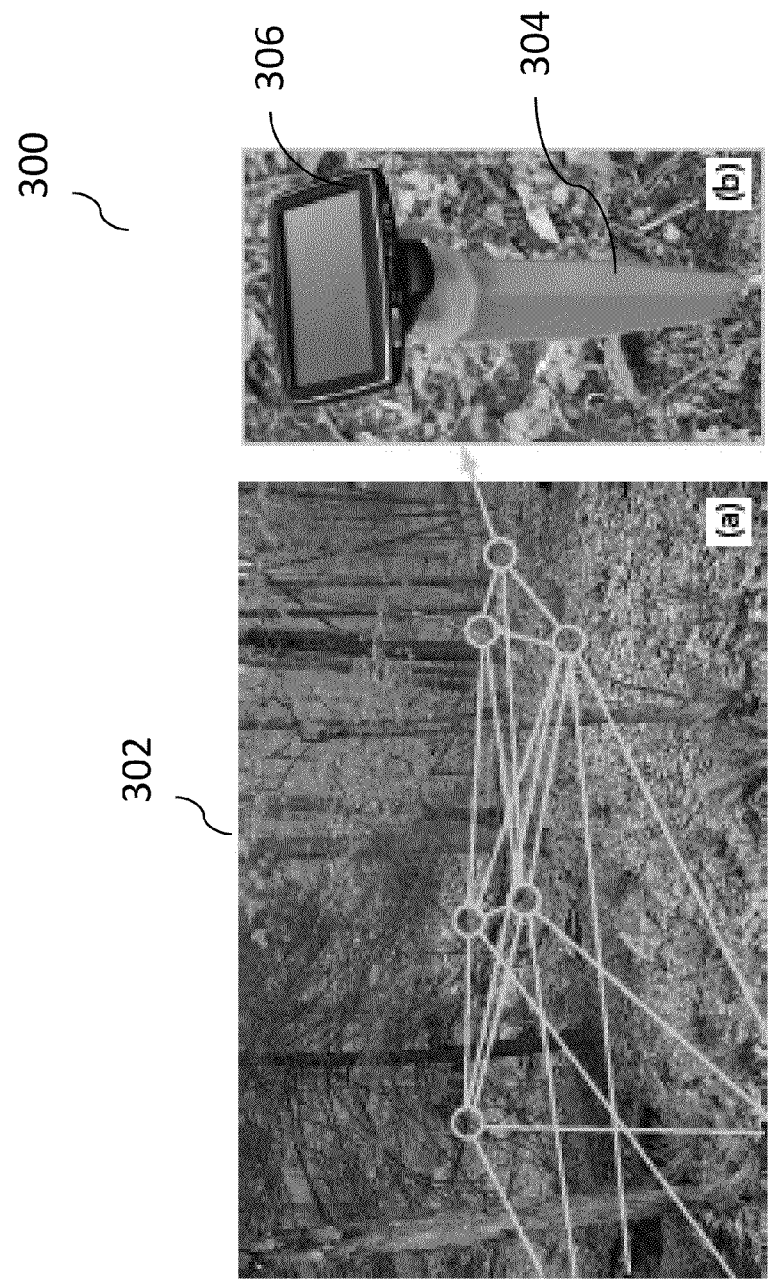
FIG. 3 illustrates an exemplary stake positioning and measurement in the system of FIG. 1, according to some implementations of the current subject matter.

In some implementations, the local site topography can be modeled with enough detail to allow for easy location of existing buildings and to support conceptual design of new buildings. To model local site topography, coordinates of various objects and/or features that are located in the site to be modeled can be obtained. Then, absolute geographical coordinates of the objects can be measured using a system of stakes that can be physically positioned on the site (e.g., which can be similar to stakes used by land surveyors). Based on the stakes, a local model of the topography defined by these stakes can be created by taking linear measurements between stakes and using such measurements to refine the obtained coordinates. An exemplary system of physical stakes 302 along with an exemplary stake 304 are shown in FIG. 3. Physical stake 304 can also include a device 306 that can determine coordinates of the stake 304 (an exemplary device can be a GPS device and/or any other device capable of determining coordinates). The distances between physical stakes 304 shown in the system 302 as circles are measured and correlated with the coordinates of stakes 304.

Figure 4:
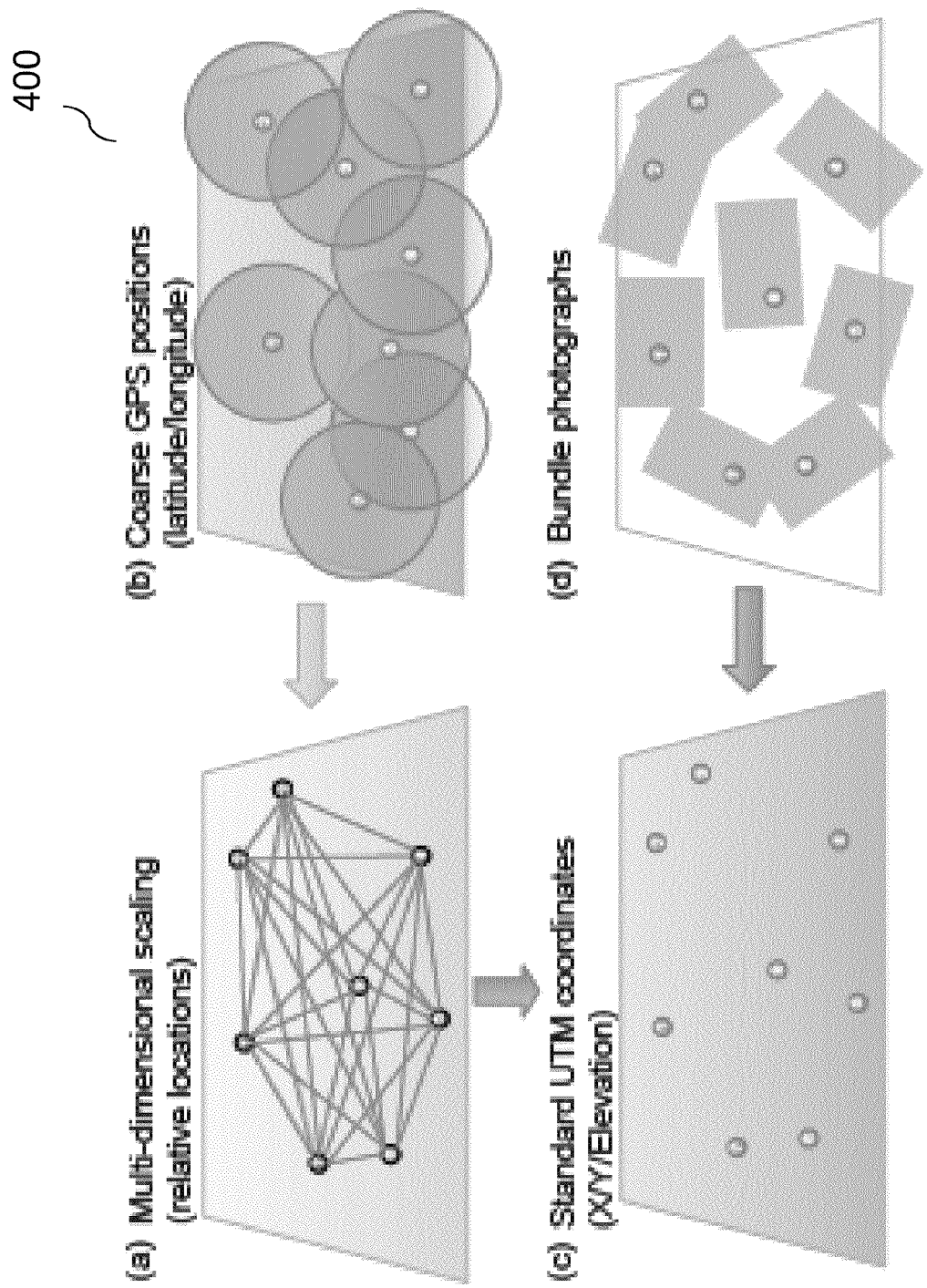
FIG. 4 illustrates an exemplary merging of data obtained from various sources corresponding to stake locations shown in FIG. 3, according to some implementations of the current subject matter.

Once the physical measurements and coordinates are correlated, linear distance measurements between all pairs of N stakes can be obtained. Multi-dimensional scaling ("MDS")

methodology can be used to find the 3D positions of the stakes (as shown in FIG. 4, part (a)). As shown in FIG. 4, in the methodology 400, pairwise distances between stakes (FIG. 4, part (a)) can be measured to estimate their relative x, y, and z coordinates with multi-dimensional scaling. The coordinates can be used to refine coarse coordinates of the stakes (FIG. 4, part (b)), resulting in more accurate global coordinates (FIG. 4, part (c)). The stakes can then used as "anchor" points to map relative positions of bundled photographs (FIG. 4, part (d)) that are taken at the site (as discussed below) into the Universal Transverse Mercator ("UTM") coordinate space. The bundling of photographs can be performed independent of the GPS/physical measurements. For example, if photograph(s) cannot be bundled with any other photograph(s) or tied to a physical stake, the photograph(s) can still generally be positioned within the scene manually. Existing pop-ups of features that can be seen in these photographs can be used as anchors. The aerial map may also provide visual cues for positioning the photographs.

Based on the above information concerning each stake, the current subject matter can estimate three-dimensional coordinates corresponding to each stake using a variety of methods. One exemplary method can involve using measurements $\delta_{i,j}$, $i,j \in N$ and estimating the unknown three-dimensional coordinates of N points $x=x_1, \ldots, x_N \in R^3$ by minimizing the following objective function $f(x)$ using non-metric MDS with Kruskal's stress criterion. $\delta_{i,j}$ can represent the measured distance from stake i to stake j (measured, for example, using a tape measure and/or any other means):

$$f(x) = \Sigma_{i<j}(\|x_i - x_j\|_2 - \delta_{i,j})^2 \quad (1)$$

The result of computing this minimum function can be a set of three-dimensional coordinates x in a local coordinate system that can be related to the global geographic coordinates in the standard UTM coordinate system (as shown in FIG. 4, part (c)). To do this, coordinates of the stakes (FIG. 4, part (b)) can be taken using a commodity device and the USGS seamless data warehouse, as well as any other sources, such as those listed above, can be queried for corresponding elevation measurements. This can generate rough standard coordinates $y=y_1, \ldots, Y_N \in R^3$. A 4-by-4 affine transform A can be estimated by minimizing the following objective function using least squares: $g(A) = \|y - Ax\|_2^2$. The transformed 3D coordinates Ax can have a higher accuracy than the commodity coordinates. In addition, this data set can include elevation at a higher accuracy.

Figure 5:
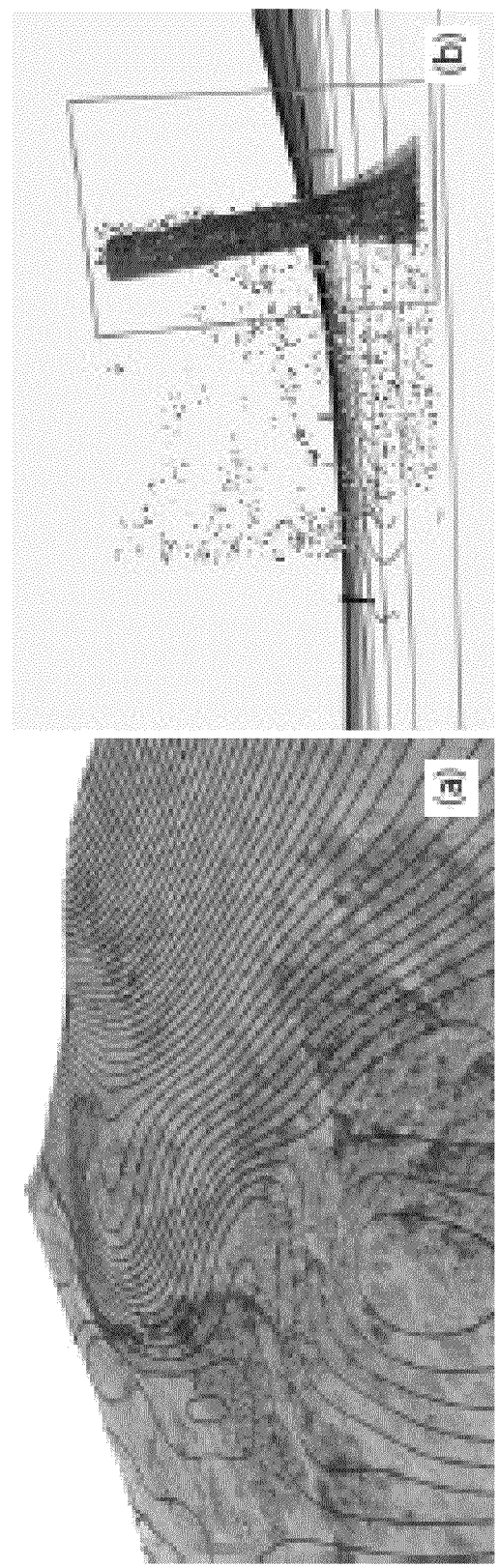
FIG. 5 illustrates an exemplary visualization of site topography, according to some implementations of the current subject matter.

The refined 3D coordinates can be merged with USGS-provided ortho-imagery (e.g., aerial photographs) and elevation data of the region, given in the form of a geo-referenced bitmap file. Other resources (e.g., Google Earth, Bing Maps, etc.) can be used as a replacement. The elevation data can be used to create a surface that is suitable for rendering through the standard graphics pipeline. The elevation data can be converted into a height-field terrain mesh, for hidden surface and line removal and user-prompted altitude queries. FIG. 5 illustrates an exemplary landscape site. In part (a) of FIG. 5, the black contour lines over an aerial photo represent elevation information at fixed intervals, where each contour represents a fixed elevation. This can provide designers with more complete geometric information about the site context, which enhances design studies. In part (b) of FIG. 5, a pop-up that can stand at the average position of feature point clouds from bundle-adjusted site photographs. The point cloud can be a set of estimated 3D points of the site geometry recovered from the bundle-adjusted photographs. The points can correspond to features that can be matched across photographs during bundle-adjustment.

Next, the site can be modeled with photographs. A number of photographs of the target site can be taken. In some implementations, photographs of the measurement stakes, site photographs, and/or any other photographs can be used so that the photographs can be positioned relative to the site topography. The current subject matter system can enable conversion of these photographs into multiple pop-ups as a lightweight visualization of the real world.

From the set of photographs, the combination of scale invariant feature transform ("SIFT") (which is a known computer algorithm to detect and describe local features in images and can be used in object recognition, robotic mapping and navigation, image stitching, 3D modeling, gesture recognition, video tracking, individual identification of wildlife and match moving, etc.) and bundle analysis can yield a set of camera intrinsic parameters/positions and sparse, noisy 3D point clouds of features. These features can include instances of stakes captured in photographs of the site (such as the photograph in FIG. 3). The relative positions of the cameras and points can be arbitrarily oriented or otherwise arranged in a predetermined orientation and/or order. Since the relative positions and orientations of cameras in a bundle of photographs is known, the photograph(s) in each bundle can be globally positioned relative to the terrain and the recovered positions of the stakes. A photograph can be aligned to the site such that the stakes within the photograph can be aligned to the positioned stakes in the scene (as described below). This can be performed either manually, semi-automatically, and/or automatically. Manual positioning can involve for example, but is not limited to, panning, zooming, orbiting, etc. the camera while looking through it at the site. In the semi-automatic positioning, global locations of the recovered stake positions can be obtained from the GPS/measurement data and/or any other information sources described above by the user confirming where the stakes are located in the photograph and then performing a least squares minimization to find the transform between the relative 3D locations of the stakes in the photograph.

A correspondence between the globally-located stakes and the local stakes (represented as a point cloud) found from the bundle adjustment of the photographs can be determined. An affine transform (which is a transformation that preserves straight lines (i.e., all points lying on a line initially still lie on a line after transformation) and ratios of distances between points lying on a straight line (e.g., the midpoint of a line segment remains the midpoint after transformation), but does not necessarily preserve angles or lengths) can be derived by minimizing the distance error between corresponding global and local stakes, with user assistance to identify the local stakes in the point cloud. Once the bundle-adjusted photographs are situated on the site topography, additional photographs can subsequently be added by the user by marking locations from a top view of the site.

Figure 6:
FIG. 6 illustrates an exemplary creation of an image pop-up in the system of FIG. 1, according to some implementations of the current subject matter.
Figure 14A:
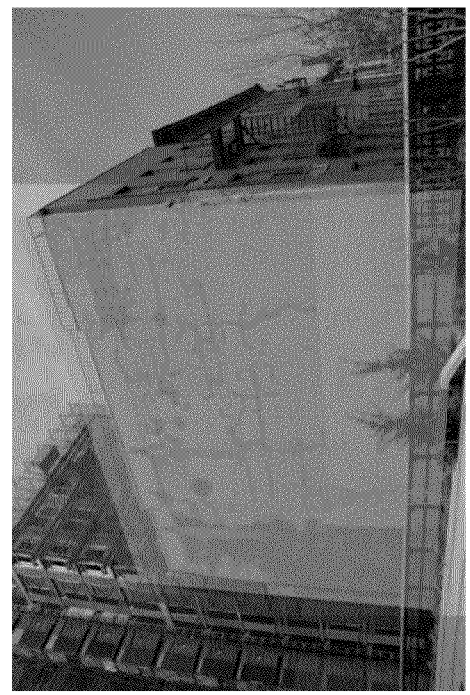
FIGS. 14a-c illustrate an exemplary creation of pop-ups, according to some implementations of the current subject matter.
Figure 14A:
Figure 14A:
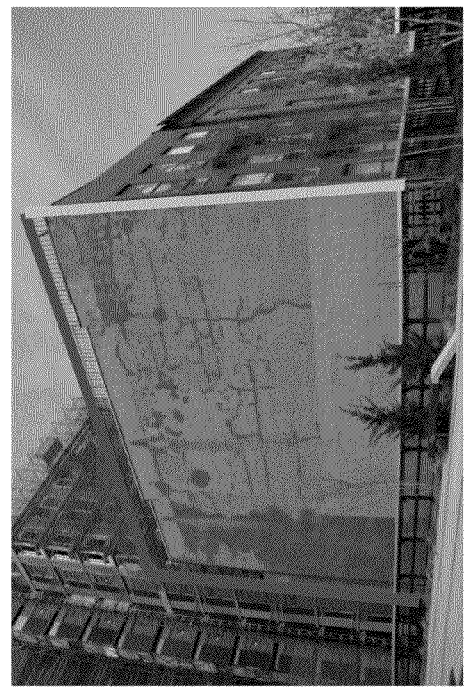
Figure 14B:
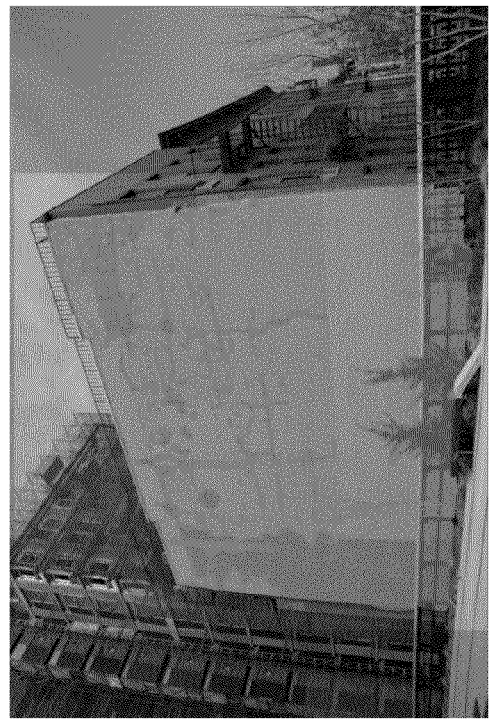
Figure 14B:
Figure 14B:
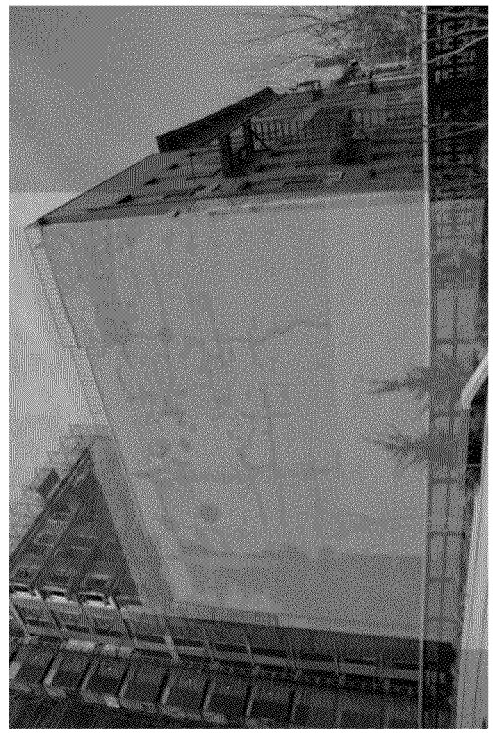
Figure 14C:
Figure 14C:
Figure 14C:

In some implementations, the obtained photographs can be converted into pop-ups. An image pop-up can include one or more components, including but not limited to, a photograph, a virtual camera, a projection plane, and a mask for the photograph. The camera parameters from the bundle adjustment can project the camera's image (the captured photograph) into one or more projection planes, or canvases, each of which can form the base of a pop-up. The parameters of each canvas can be influenced by the outline of the corresponding pop-up (stored as a mask for the photograph) (as shown in FIG. 6, part (a)). The initial outline can be specified using an interactive image-segmentation tool, as shown in FIG. 6, part (b). This can allow the user to highlight significant site features, either through painting, or using free-form connected strokes or lines. The user can make refinements to the outline using a known interactive foreground extraction graph-cut algorithm and an edge-respecting brush. FIGS. 14a-c illustrate an exemplary process for creating a pop-up. The process can begin by the user defining a rough 2D outline of the pop-up through freeform connected lines and strokes, as shown in FIG. 14a (as represented by the solid lines in the left-hand side of FIG. 14a). Once the rough 2D outline of the pop-up is defined, it can be refined. Refinements of the outline can be done automatically using a known foreground extraction graph-cut algorithm (an exemplary graph-cut algorithm is shown in FIG. 14b and discussed in Rother, C., Kolmogorov, V., and Blake, A., "Grabcut: Interactive Foreground Extraction Using Iterated Graph Cuts," ACM Trans. Graph. 23 (August 2004), pp. 309-314) or interactively by painting a refined outline using an edge-respecting brush (as shown in FIG. 14c and discussed in Olsen, D. R., Jr. and Harris, M. K., "Edge-Respecting Brushes," Proceedings of The 21$^{st}$ Annual ACM Symposium on User Interface Software and Technology (UIST '08), ACM, 2008, pp. 171-180). Other methods for creating pop-ups can be used and the current subject matter is not limited to the above-discussed methods.

Once the pop-up outline is finalized, a determination can be made as to which points originated from the area of the photograph enclosed by the outline. The depth and orientation of the pop-up's canvas can then be found using least squares optimization using these points, as shown in FIGS. 5 and 6. The canvas can have the same properties as a sketching canvas. If the depth of the canvas is computed incorrectly, the user can transform the canvas to the correct position and orientation and the pop-up can be re-projected instantaneously. While a dense set of photographs can be useful for the bundling calculations, once camera positions are determined, large numbers of photographs can be discarded as not useful. Further, not every feature (e.g., every twig, rock, etc.) may need to be represented as an individual pop-up. The most significant views and features can depend on the user's impression of the site, user's design goals, personal preferences, etc. The user can select an appropriate set of photographs and features for achieving optimal site visualization. Determination and removal of features that may be less important can be involved in the creation of pop-ups (creation of pop-ups is discussed above and shown in FIGS. 14a-c). For example, rather than having the entire photograph as a single pop-up, the user can outline or cut out certain portions, features, objects, image segments, etc. that the user can be interested in using in the site representation and then use only those portions, features, objects, image segments, etc. to create one or more pop-ups, projected onto one or more different canvases. This can eliminate other portions, features, objects, image segments, etc. in the photographs that are not selected by the user.

Figure 8:
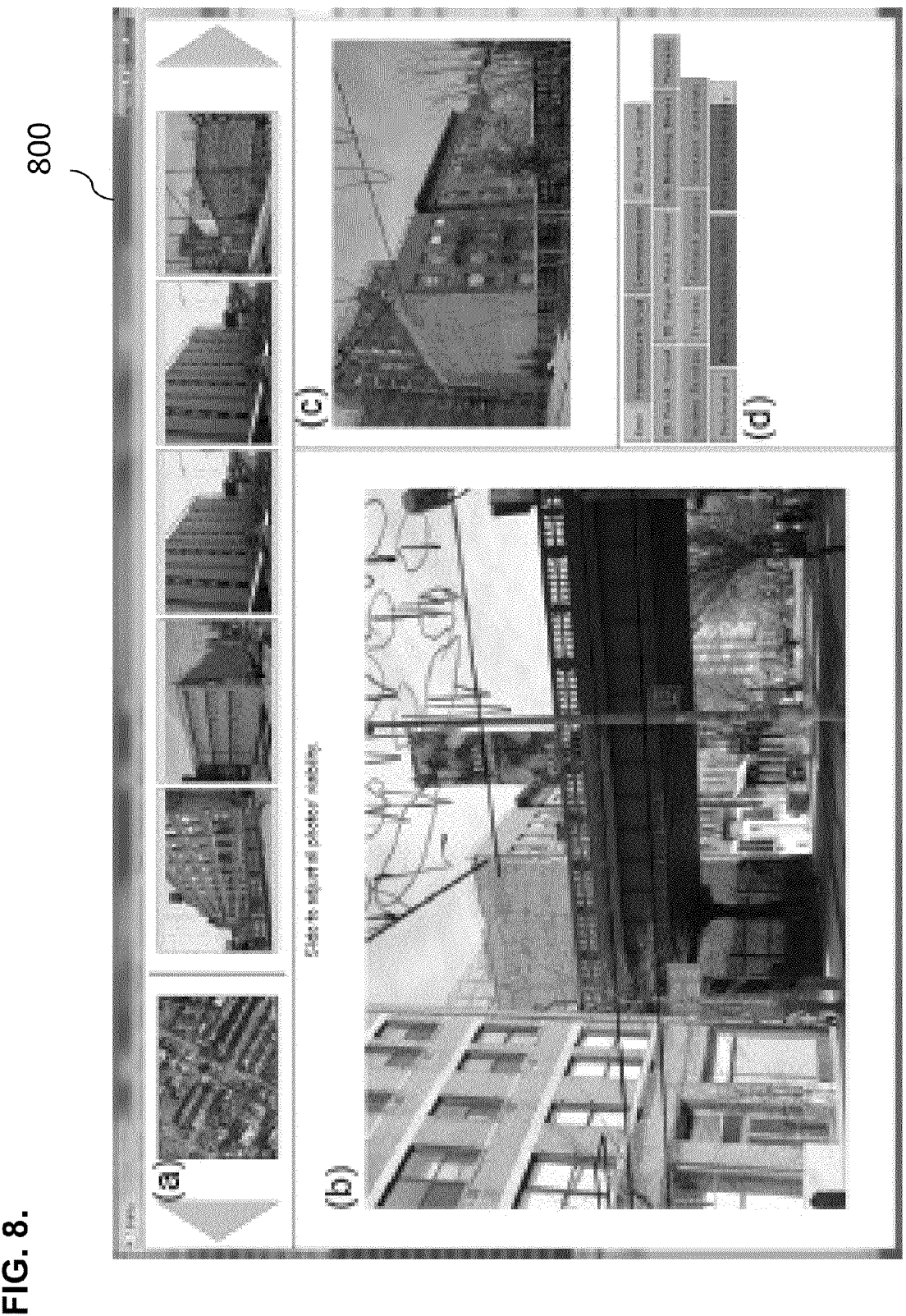
FIG. 8 illustrates an exemplary sketching interface of the system of FIG. 1, according to some implementations of the current subject matter.
Figure 9A:
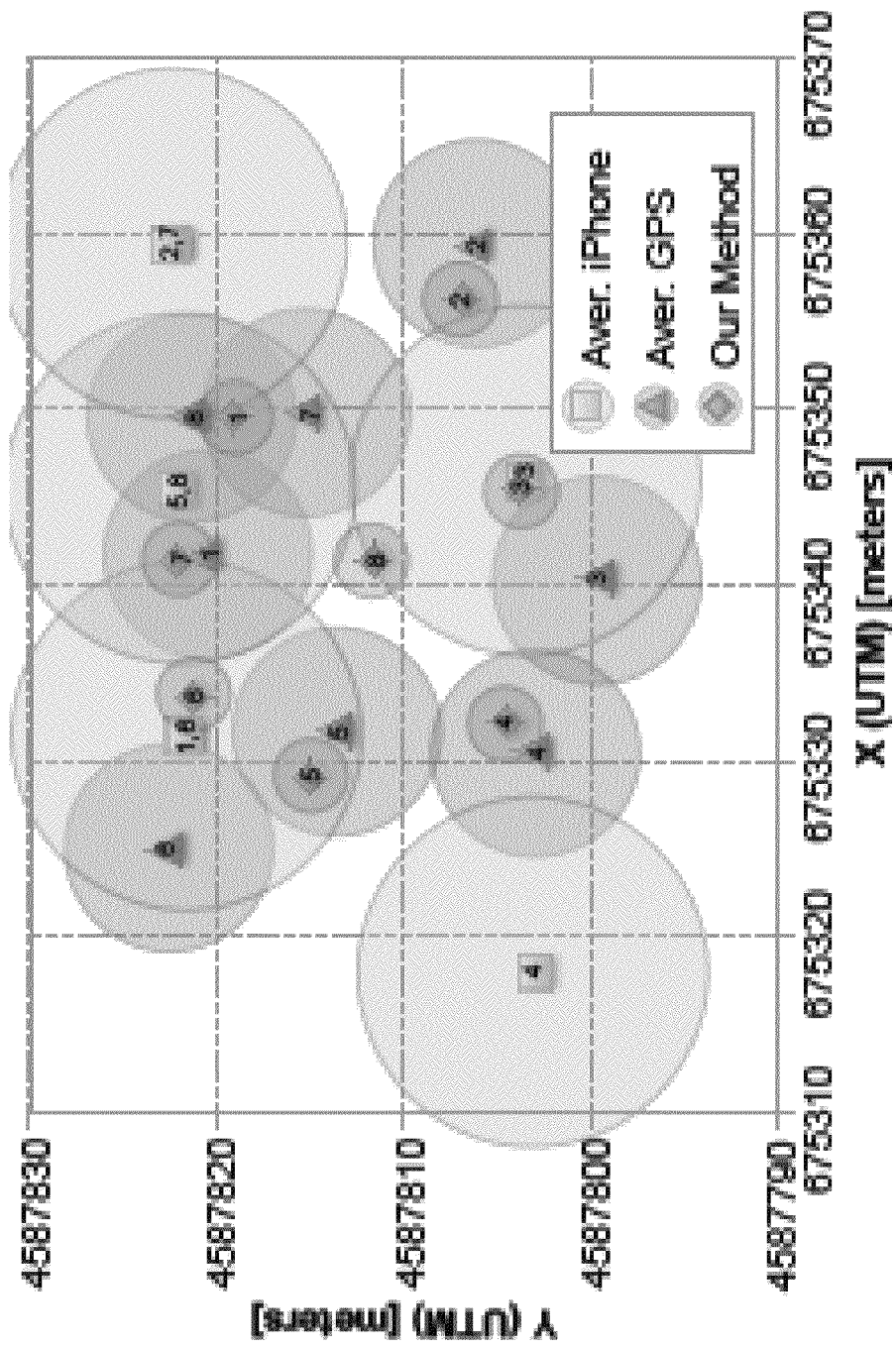
FIGS. 9a-11 illustrate an experimental example conducted using the system of FIG. 1, according to some implementations of the current subject matter.
Figure 9B:
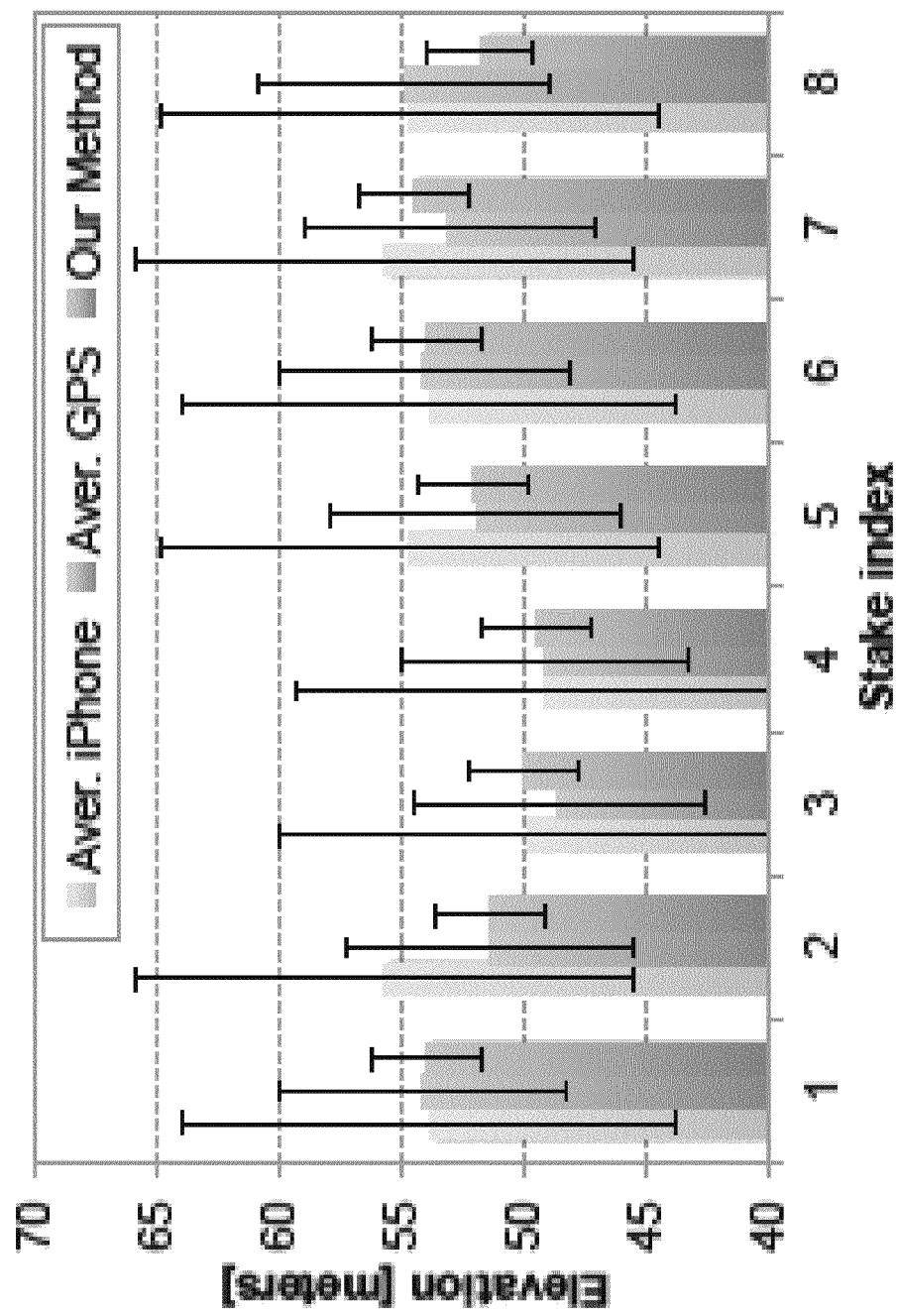

Once the site environment representation is generated, it can be incorporated into a sketching system for conceptual design. A sketching interface can be provided for performing such incorporation and can allow free-viewpoint navigation and the ability to view occlusions and other spatial effects. In some implementations, the sketching system can include a variety of functionalities, including at least one of canvas positioning functionality, 3D context functionality, scaling functionality, viewpoint/bookmark functionality, camera motion functionality, site environment visualization functionality, and stroke functionality. An exemplary sketching interface 800 is illustrated in FIG. 8. The interface can include navigation bookmarks (aerial/site views) (FIG. 8, part (a), a main sketching window (FIG. 8, part (b)), a secondary window displaying the site from a different viewpoint (FIG. 8, part (c)), and a control panel for displaying functionalities of the system (FIG. 8, part (d)). The sketching interface can include any other components and/or features.

In some implementations, the sketching system can be a canvas that is displayed as a rectangle that can expand or contract to hold the strokes that can be drawn on it. The canvas can be positioned and oriented in a 3D space. Individual strokes can be projectively transferred from one canvas to another to evolve a 3D structure from individual 2D sketches. Images and/or pieces of images, created in the popup process, can be added to strokes and can be similarly projected onto canvases. The site topography can be presented as both a textured mesh and as strokes following elevation isolines or contour lines attached to canvases.

The sketching system can include canvas positioning tools that can position canvases containing sketches relative to the representation of the environment. New canvases can be positioned relative to a stroke drawn on an existing canvas (representing the approximate intersection of the two planes). The user can move a canvas by dragging its intersection line with any other canvas. The sketching system can also include at least one cue that shows where canvases intersect each other as well as a cue that represents the ground.

In some implementations, the 3D context functionalities can allow the user to create at least one image pop-up to give the user a view of the site environment and to draw with occlusions in that view. The sketching system can also allow the user to examine views that can be close to the initial view. The system can create multiple image pop-ups to represent the environmental context that can be placed into relative positions using an image bundling system.

In some implementations, the sketching system can include a scaling functionality that can provide a visual model of the site environment with approximate positioning relative to a representation of the site topography. It can also include quantitative information about the site, contextual information presented in meaningful physical length scales. In some implementations, to provide appropriate scaling, a geographical positioning method tied to a global coordinate system can be used as discussed above. The system can also estimate overall sizes of bounding boxes of designed objects. In some implementations, scaling can mean that the bundle-adjusted camera positions, GPS/stake measurements, terrain input, etc., are all in physical coordinates in the recreated site. In other words, distances between site objects within the virtual site can approximately correspond to the physical distances between these objects.

In some implementations, the sketching system can also include viewpoints and bookmarks that can allow users to view both the site environment and the designed structure together from a single point of view. In some implementations, the user can also see multiple views simultaneously. The user can also be provided with a functionality to bookmark various views throughout the site design process. The sketching system can show a main and a subsidiary window to visualize the site from two viewpoints simultaneously and can include easily-accessible bookmark list with thumbnails of additional views (including an aerial view) on the top of the interface.

In some implementations, the sketching system can also provide a camera motion functionality that allows simulation of how to move through and interact with the structure being designed. The camera motion functionality can also provide optional camera motion between two predefined viewpoints. By selecting a bookmark, popup or canvas, the user can be automatically transported to the bookmarked view, parent view of the pop-up, or head-on view of the canvas, respectively. Intermediate camera parameters can be found by interpolating the initial and final camera poses. Terrain altitude queries can be performed to prevent any intermediate camera poses from being underneath the ground.

Figure 7:
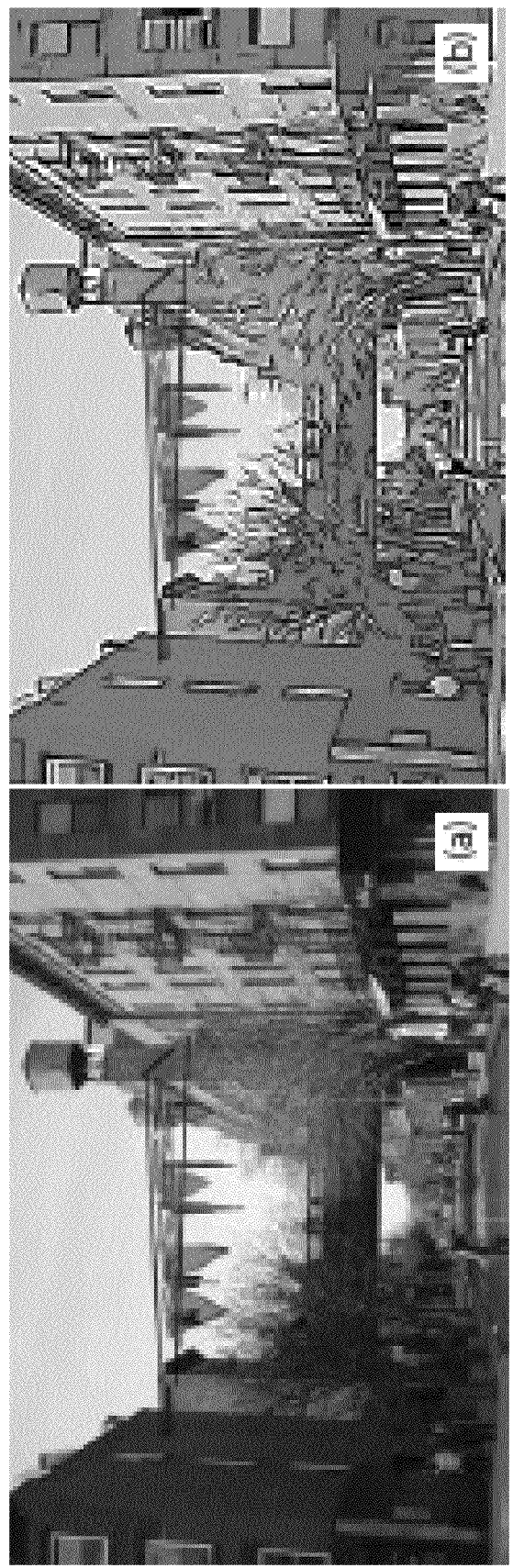
FIG. 7 illustrates an exemplary preliminary sketch using the system of FIG. 1, according to some implementations of the current subject matter.

In some implementations, the sketching system can include environment visualization functionality that provides site visualizations that are harmonious with the user's pen strokes. Such functionality can be accomplished through known non-photorealistic rendering ("NPR") visualization tools. The environment visualization functionality can allow the user to adjust the appearance of the site environment to the user's sketch. The contrast between pop-ups and the sketch can be adjusted by changing color saturation. The quantization of colors in pop-ups can be adjusted to give a more painterly effect. Pop-ups can also be selectively hidden if any of them are distracting when seen from a particular view, such as when a pop-up is in between the viewing camera and the sketch. The user can have the system generate strokes on a pop-up's canvas corresponding to edges in its texture. The user can adjust the sensitivity of the edge detection to vary the number and detail of strokes. Strokes can be generated in real time, so that the user can quickly browse options to pick the one closest to their intent. To convert the edge image into strokes known conversion techniques can be used. FIG. 7 illustrates a comparison between two visualizations. Part (a) of FIG. 7 illustrates a photographic representation of the site and part (b) of FIG. 7 illustrates the same site but represented using NPR visualization tools. These style adjustments can be done per pop-up or for all of them at once. The style of the terrain display can also be adjusted—from an aerial photo of the site to a textured hill elevation. During the design process, the user can also work with photograph(s) because they offer a more realistic sense of the space being designed, which can allow for better understanding of the surrounding environment.

In some implementations, the sketching system can also include stroke functionality, where the stroke can be a monochromatic stroke, an all-black stroke, a color stroke, as well as any other stroke. The functionality can also include a color brush to paint a surface. The user can also select color of the stroke while working on the site design, which allows for a more creative control of the design. The painted occlusions can add texture and depth to the user's designs.

Experimental Example

The following is a discussion of an experiment conducted using the current subject matter's sketching system. The discussion compares three different positioning methods related to the site modeling approach described above. During this experiment, the current subject matter methodology has been applied to two distinct sites—a rural site and an urban site. FIGS. 9a-13 illustrate implementation of the current subject matter's methodology as well as results of this experimentation.

During this experiment, an accuracy of three positioning methods was compared. The positioning methods included: (1) use of raw iPhone 4 GPS readings, (2) use of readings from a TomTom XL satellite navigation system, and (3) use of the TomTom readings refined by our MDS method. The methods were used to determine 3D geographic location estimates (metric UTM and elevation coordinates) in the rural site (approximate dimensions 60×60 $m^2$). A set of 8 stakes was used within the site, where the stakes were disposed on the site using measured, pairwise distances between the stakes as ground-truth values. The median errors for the pairwise stake distances were 10.12 m, 5.93 m and 2.20 m for the iPhone, TomTom, and MDS methods, respectively. These are indicated by the circle boundaries in FIG. 9(a) and error bars in FIG. 9(b). The results indicate that the relative distances between stakes are better maintained by estimating locations using the inventors' current method, rather than using iPhone or TomTom readings directly.

As stated above, the current subject matter system was used for designing both the rural and urban sites. In the case of the rural setting (where the topography is more relevant), the site had a complex site layout and online resources (such as models stored on Google Earth) to represent the site's features were not readily available. In the case of the urban setting (where the topography is less relevant), the site was designed to include a free-form shape of the sculpture that was intended to be compatible with the full existing urban setting, which could not easily be sketched out in Google SketchUp or other CAD systems.

Figure 10:
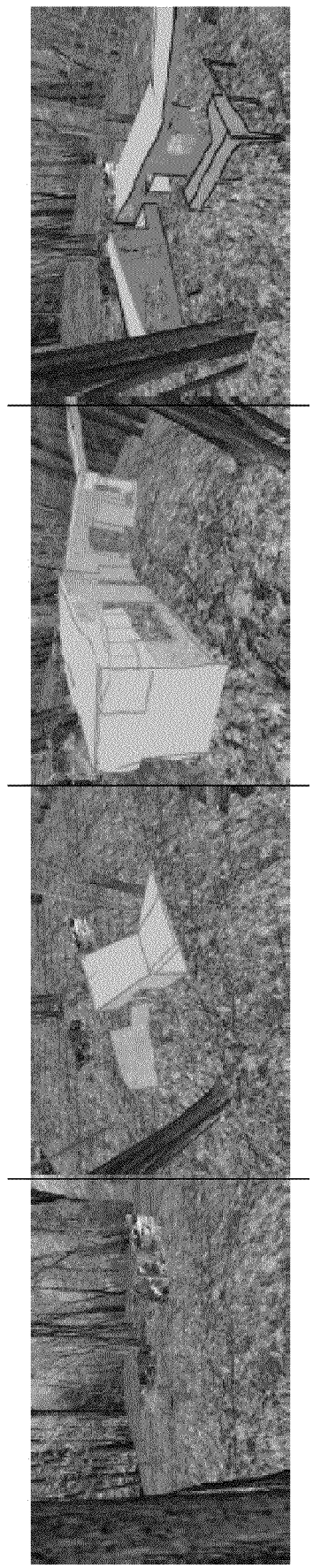
Figure 11:

The rural site is a house in the woods illustrated in FIG. 10-11. The site is a sloping, densely wooded lot. One objective of the design was to place the structure in the landscape in a minimally-invasive way, thereby leaving most of the natural features intact. The massing of the design, which consists of two main wings and an overall shape that is low to the ground, is responsive to the topography of the site, tightly conforming to the slope. Note that the buildings are occluded by trees. This site was modeled using approximately 60 photographs, from a total of roughly 400 taken. Approximately 30 photos were bundled, most of which were treated as "anchors," around which other individual photos were positioned as needed. 10 photographs were used in the background. Entire photos were used as a backdrop. The total site surveying time was about 4 hours. The modeling time, which included some experimentation with applying texture to the terrain, took approximately 7 hours.

Figure 12:
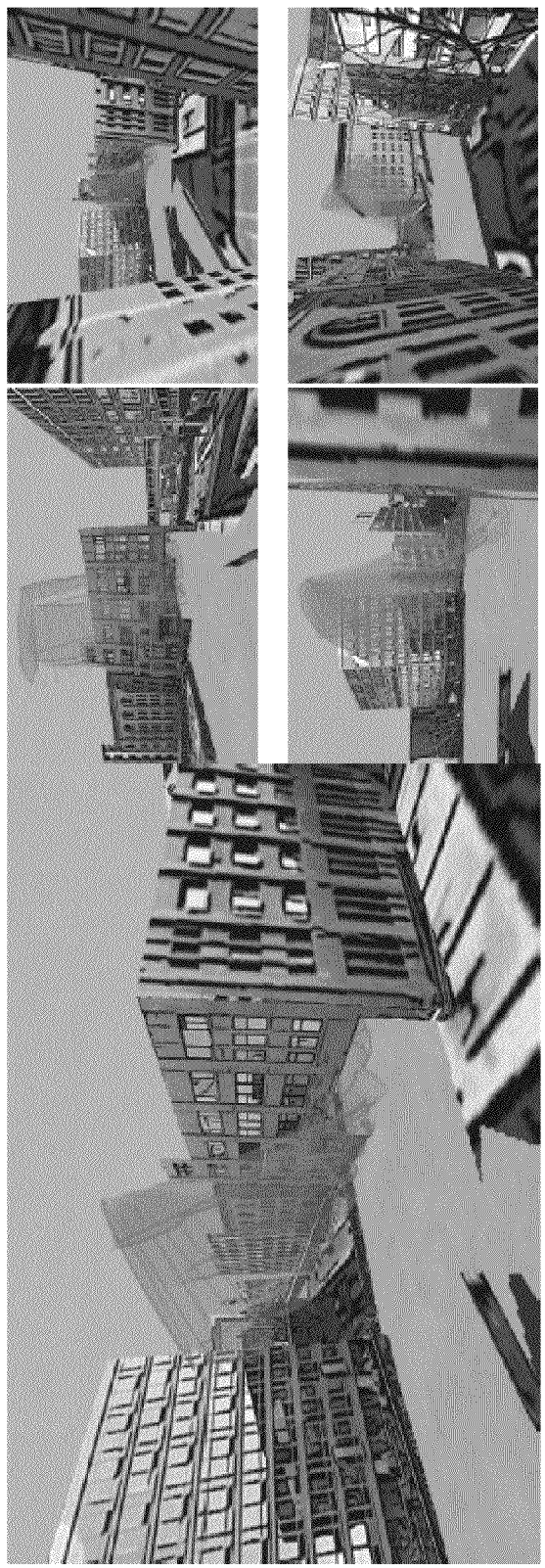
FIGS. 12-13 illustrate another experimental example conducted using the system of FIG. 1, according to some implementations of the current subject matter.
Figure 13:
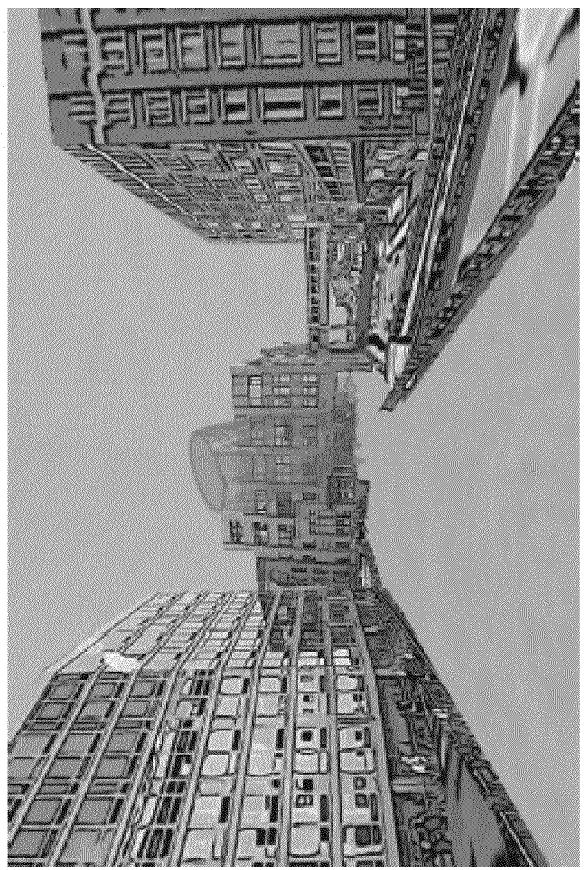
Figure 13:

The urban site was a sculpture over the high line and is illustrated in FIGS. 12-13. It illustrates an architectural-scale sculpture over the High Line Park in New York City's Chelsea district. The High Line, which sits three stories above street level and snakes its way through the dense fabric of the west side of Manhattan, is a public park, built as a transformation of an elevated, derelict railroad track. The park offers views of the buildings that line the park, as well as expansive views of the surrounding cityscape. The proposed sculpture includes a mesh armature system combined with flexible volumetric forms made of knotted high-technology fabric, and will be suspended from adjacent building using Spectra ropes. The design, shown in FIGS. 12-13 is influenced by the surrounding context. Thus, the ability to sketch freely in this context offers a unique understanding of the context, as well as a means to develop the design. In particular, in order to appreciate and relate effectively to the context, initial sketches were created on linked pop-ups showing a full view of the scene. The proposed design rises from the site and cantilevers over the rail beds, embracing the existing track, and snakes under an existing building. Additionally, the structure aims to create cinematic views of the cityscape. By draping and fitting the structure to the existing rail bed, the sculpture will be tightly tied to its surrounding buildings.

To create this site, approximately 45 digital photos were used, from a total of about 400. Here, fewer than five bundled photos were used, as most of the photographs were of individual building facades, and the regularity of the building structures, combined with the help of the aerial view, made individual positioning relatively easy. In addition, six background photos were used. No stakes or measurements were used here, although spot measurements of the height and width of the High Line would likely have been helpful in retrospect. The total surveying time was 2 hours, while the total modeling time was about 5 hours.

In both sites, approximately 70% of the photos for creating pop-ups and the remaining 30%, either for verifying alignments or for interesting views. The landscape site was fully enclosed with the background pop-ups, whereas this was unnecessary within the High Line site, owing to the very different nature of the visibility conditions posed by the cityscape.

Figure 15:
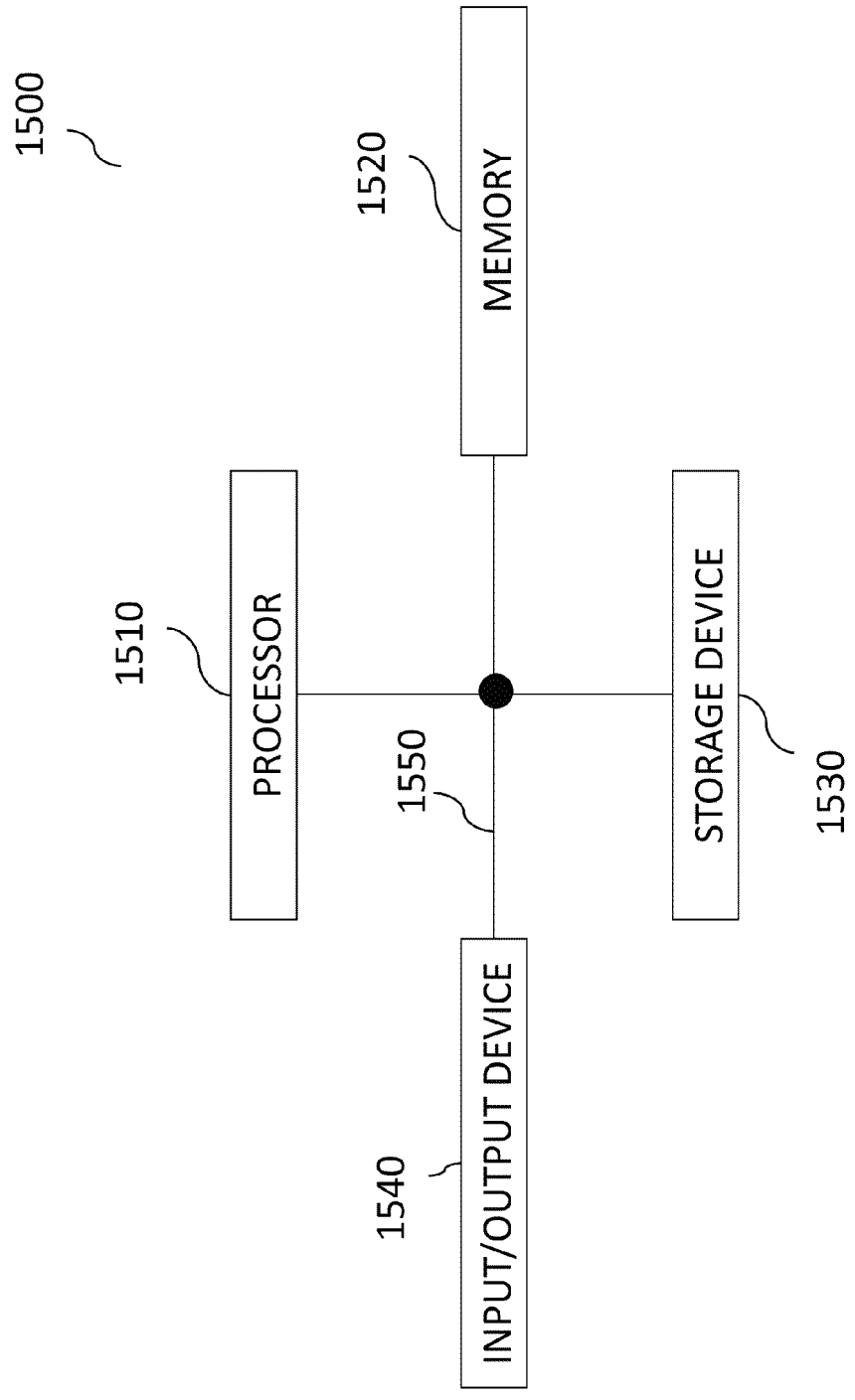
FIG. 15 illustrates an exemplary system, according to some implementations of the current subject matter.

In some implementations, the current subject matter can be configured to be implemented in a system 1500, as shown in FIG. 15. The system 1500 can include a processor 1510, a memory 1520, a storage device 1530, and an input/output device 1540. Each of the components 1510, 1520, 1530 and 1540 can be interconnected using a system bus 1550. The processor 1510 can be configured to process instructions for execution within the system 1500. In some implementations, the processor 1510 can be a single-threaded processor. In alternate implementations, the processor 1510 can be a multi-threaded processor. The processor 1510 can be further configured to process instructions stored in the memory 1520 or on the storage device 1530, including receiving or sending information through the input/output device 1540. The memory 1520 can store information within the system 1500. In some implementations, the memory 1520 can be a computer-readable medium. In alternate implementations, the memory 1520 can be a volatile memory unit. In yet some implementations, the memory 1520 can be a non-volatile memory unit. The storage device 1530 can be capable of providing mass storage for the system 1500. In some implementations, the storage device 1530 can be a computer-readable medium. In alternate implementations, the storage device 1530 can be a floppy disk device, a hard disk device, an optical disk device, a tape device, non-volatile solid state memory, or any other type of storage device. The input/output device 1540 can be configured to provide input/output operations for the system 1500. In some implementations, the input/output device 1540 can include a keyboard and/or pointing device. In alternate implementations, the input/output device 1540 can include a display unit for displaying graphical user interfaces. The system can also contain a graphical processing unit.

Figure 16:
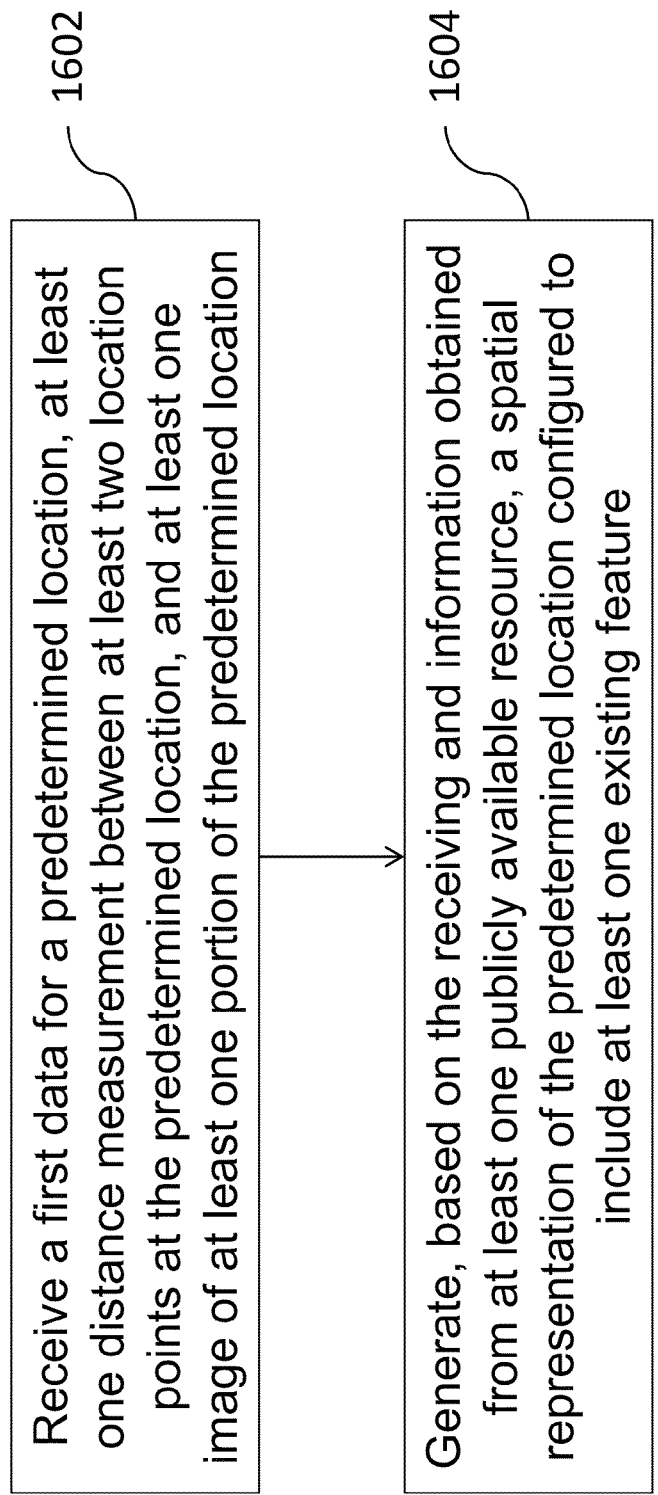
FIG. 16 illustrates an exemplary method, according to some implementations of the current subject matter.

FIG. 16 illustrates an exemplary method 1600, according to some implementations of the current subject matter. At 1602, a first data for a predetermined location (for example, but not limited to, geographic data, exterior measurement data, GPS data, interior measurement data (such as measurements for interiors of buildings, rooms, etc.), and/or any other data), at least one distance measurement between at least two location points at the predetermined location, and at least one image of at least one portion of the predetermined location can be received. At 1604, a spatial representation of the predetermined location configured to include at least one existing feature can be generated based on the receiving and information obtained from at least one publicly available resource. The spatial representation of the predetermined location can include a detailed representation of the at least one portion of the predetermined location having the at least one existing feature. At least one of the receiving and the generating can be performed using at least one processor.

In some implementations, the current subject matter can include at least one or more of the following optional features. At least one image of the at least one portion can be obtained using an image capturing device disposed at least one location point at the predetermined location. The first data for the predetermined location can include a geographic elevation data.

The generating can include merging the first data for the predetermined location, the at least one distance measurement between at least two location points at the predetermined location, and the at least one image of the at least one portion of the predetermined location and generating at least one user interface for allowing a user to edit the merged first data for the predetermined location, the at least one distance measurement between at least two location points at the predetermined location, and the at least one image of the at least one portion of the predetermined location.

The generated spatial representation of the predetermined location can include a lightweight representation of an environment at the predetermined location.

The spatial representation of the predetermined location can be a three-dimensional representation of the predetermined location.

The method can also include generating at least one new feature based on the at least one existing feature contained within the spatial representation of the predetermined location.

At least one location point at the predetermined location can be configured to define a relative positioning of at least one image of at least one portion at the predetermined location.

In some implementations, the method further includes obtaining at least one additional image of the at least one portion of the predetermined location, merging the first data for the predetermined location, the at least one distance measurement between at least two location points at the predetermined location, the at least one image of the at least one portion of the predetermined location, and the at least one additional image of the at least one portion of the predetermined location, and generating at least one user interface for allowing a user to edit the merged first data for the predetermined location, the at least one distance measurement between at least two location points at the predetermined location, the at least one image of the at least one portion of the predetermined location, and the at least one additional image of the at least one portion of the predetermined location. The method can also include adding at least one drawing stroke to the merged first data for the predetermined location, the at least one distance measurement between at least two location points at the predetermined location, the at least one image of the at least one portion of the predetermined location, and the at least one additional image of the at least one portion of the predetermined location.

In some implementations, the method can also include correcting received first data using the at least one distance measurement between at least two location points at the predetermined location.

The systems and methods disclosed herein can be embodied in various forms including, for example, a data processor, such as a computer that also includes a database, digital electronic circuitry, firmware, software, or in combinations of them. Moreover, the above-noted features and other aspects and principles of the present disclosed implementations can be implemented in various environments. Such environments and related applications can be specially constructed for performing the various processes and operations according to the disclosed implementations or they can include a general-purpose computer or computing platform selectively activated or reconfigured by code to provide the necessary functionality. The processes disclosed herein are not inherently related to any particular computer, network, architecture, environment, or other apparatus, and can be implemented by a suitable combination of hardware, software, and/or firmware. For example, various general-purpose machines can be used with programs written in accordance with teachings of the disclosed implementations, or it can be more convenient to construct a specialized apparatus or system to perform the required methods and techniques.

The systems and methods disclosed herein can be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

As used herein, the term "user" can refer to any entity including a person or a computer.

Although ordinal numbers such as first, second, and the like can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the invention, which is defined by the scope of the appended claims. Other implementations are within the scope of the following claims.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user can provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input.

The subject matter described herein can be implemented in a computing system that includes a back-end component, such as for example one or more data servers, or that includes a middleware component, such as for example one or more application servers, or that includes a front-end component, such as for example one or more client computers having a graphical user interface or a Web browser through which a user can interact with an implementation of the subject matter described herein, or any combination of such back-end, middleware, or front-end components. The components of the system can be interconnected by any form or medium of digital data communication, such as for example a communication network. Examples of communication networks include, but are not limited to, a local area network ("LAN"), a wide area network ("WAN"), and the Internet.

The computing system can include clients and servers. A client and server are generally, but not exclusively, remote from each other and typically interact through a communication network. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations can be within the scope of the following claims.

What is claimed:

1. A computer implemented method comprising:
receiving a first data for a predetermined location, at least one linear distance measurement between at least two location points at the predetermined location, and at least one image of at least one portion of the predetermined location;
generating, based on the receiving and information obtained from at least one publicly available resource, a spatial representation of the predetermined location configured to include at least one existing feature;
wherein the spatial representation of the predetermined location includes a three-dimensional detailed representation of the at least one portion of the predetermined location having the at least one existing feature, the spatial representation being generated based on a plurality of lightweight representations of an environment at the predetermined location each containing a minimum number of elements for describing the environment at the predetermined location, the plurality of lightweight representations are positioned in a three-dimensional space based on the received first data, the at least one linear distance measurement, and the at least one image to generate the spatial representation; and
performing at least one change to the at least one lightweight representation in the plurality of lightweight representations and a three-dimensional detailed representation to generate the spatial representation;
wherein at least one of the receiving, the generating, and the performing are performed using at least one processor.

2. The method according to claim 1, wherein the at least one image of the at least one portion is obtained using an image capturing device disposed at least one location point at the predetermined location.

3. The method according to claim 1, wherein the first data for the predetermined location includes a geographic elevation data.

4. The method according to claim 1, wherein the generating further comprises
generating at least one user interface for allowing a user to edit at least one of the following: the first data for the predetermined location, the at least one distance measurement between at least two location points at the predetermined location, the at least one image of the at least one portion of the predetermined location, and at least one combination thereof.

5. The method according to claim 1, wherein the lightweight representation is configured to minimize a number of lightweight characteristics used to generate the detailed representation of the at least one portion of the predetermined location;
the lightweight characteristics include at least one of the following: a polygon, a texture, a line, a photograph, and a graphical image;
the lightweight representation is configured to be stored in a memory coupled to the at least one processor and configured to consume an amount of memory that is less than an amount of memory consumed by the spatial representation.

6. The method according to claim 1, wherein the spatial representation of the predetermined location is a three-dimensional representation of the predetermined location.

7. The method according to claim 1, further comprising generating at least one new feature based on the at least one existing feature contained within the spatial representation of the predetermined location.

8. The method according to claim 1, wherein at least one location point at the predetermined location is configured to define a relative positioning of at least one image of at least one portion at the predetermined location.

9. The method according to claim 4, further comprising
obtaining at least one additional image of the at least one portion of the predetermined location; and
generating at least one user interface for allowing the user to edit at least one of the following: the first data for the predetermined location, the at least one distance measurement between at least two location points at the predetermined location, the at least one image of the at least one portion of the predetermined location, the at least one additional image of the at least one portion of the predetermined location, and at least one combination thereof.

10. The method according to claim 9, further comprising adding at least one drawing stroke to the merged first data for the predetermined location, the at least one distance measurement between at least two location points at the predetermined location, the at least one image of the at least one portion of the predetermined location, and the at least one additional image of the at least one portion of the predetermined location.

11. The method according to claim 1, further comprising correcting received first data using the at least one distance measurement between at least two location points at the predetermined location.

12. A system comprising:
at least one programmable processor; and
a machine-readable medium storing instructions that, when executed by the at least one programmable processor, cause the at least one programmable processor to perform operations comprising:
receiving a first data for a predetermined location, at least one linear distance measurement between at least two location points at the predetermined location, and at least one image of at least one portion of the predetermined location;
generating, based on the receiving and information obtained from at least one publicly available resource, a spatial representation of the predetermined location configured to include at least one existing feature;
wherein the spatial representation of the predetermined location includes a three-dimensional detailed representation of the at least one portion of the predetermined location having the at least one existing feature, the spatial representation being generated based on a plurality of lightweight representations of an environment at the predetermined location each containing a minimum number of elements for describing the environment at the predetermined location, the plurality of lightweight representations are positioned in a three-dimensional space based on the received first data, the at least one linear distance measurement, and the at least one image to generate the spatial representation; and
performing at least one change to the at least one lightweight representation in the plurality of lightweight representations and a three-dimensional detailed representation to generate the spatial representation.

13. The system according to claim 12, wherein the at least one image of the at least one portion is obtained using an image capturing device disposed at least one location point at the predetermined location.

14. The system according to claim 12, wherein the first data for the predetermined location includes a geographic elevation data.

15. The system according to claim 12, wherein the generating further comprises
generating at least one user interface for allowing a user to edit at least one of the following: the first data for the predetermined location, the at least one distance measurement between at least two location points at the predetermined location, the at least one image of the at least one portion of the predetermined location, and at least one combination thereof.

16. The system according to claim 12, wherein the spatial representation of the predetermined location is a three-dimensional representation of the predetermined location.

17. The system according to claim 12, wherein the lightweight representation is configured to minimize a number of lightweight characteristics used to generate the detailed representation of the at least one portion of the predetermined location;
the lightweight characteristics include at least one of the following: a polygon, a texture, a line, a photograph, and a graphical image;
the lightweight representation is configured to be stored in a memory coupled to the at least one programmable processor and configured to consume an amount of memory that is less than an amount of memory consumed by the spatial representation.

18. The system according to claim 12, wherein the operations further comprise
generating at least one new feature based on the at least one existing feature contained within the spatial representation of the predetermined location.

19. The system according to claim 12, wherein at least one location point at the predetermined location is configured to define a relative positioning of at least one image of at least one portion at the predetermined location.

20. The system according to claim 15, wherein the operations further comprise
obtaining at least one additional image of the at least one portion of the predetermined location; and
generating at least one user interface for allowing the user to edit at least one of the following: the first data for the predetermined location, the at least one distance measurement between at least two location points at the predetermined location, the at least one image of the at least one portion of the predetermined location, the at least one additional image of the at least one portion of the predetermined location, and at least one combination thereof.

21. The system according to claim 20, wherein the operations further comprise
adding at least one drawing stroke to the merged first data for the predetermined location, the at least one distance measurement between at least two location points at the predetermined location, the at least one image of the at least one portion of the predetermined location, and the at least one additional image of the at least one portion of the predetermined location.

22. The system according to claim 12, wherein the operations further comprise
correcting received first data using the at least one distance measurement between at least two location points at the predetermined location.

23. A computer program comprising a non-transitory machine-readable medium storing instructions that, when executed by at least one programmable processor, cause the at least one programmable processor to perform operations comprising:
receiving a first data for a predetermined location, at least one linear distance measurement between at least two location points at the predetermined location, and at least one image of at least one portion of the predetermined location;
generating, based on the receiving and information obtained from at least one publicly available resource, a spatial representation of the predetermined location configured to include at least one existing feature;
wherein the spatial representation of the predetermined location includes a three-dimensional detailed representation of the at least one portion of the predetermined location having the at least one existing feature, the spatial representation being generated based on a plurality of lightweight representations of an environment at the predetermined location each containing a minimum number of elements for describing the environment at the predetermined location, the plurality of lightweight representations are positioned in a three-dimensional space based on the received first data, the at least one linear distance measurement, and the at least one image to generate the spatial representation; and
performing at least one change to the at least one lightweight representation in the plurality of lightweight representations and a three-dimensional detailed representation to generate the spatial representation.

24. The computer program product according to claim 23, wherein the at least one image of the at least one portion is obtained using an image capturing device disposed at least one location point at the predetermined location.

25. The computer program product according to claim 23, wherein the first data for the predetermined location includes a geographic elevation data.

26. The computer program product according to claim 23, wherein the generating further comprises
generating at least one user interface for allowing a user to edit at least one of the following: the first data for the predetermined location, the at least one distance measurement between at least two location points at the predetermined location, and the at least one image of the at least one portion of the predetermined location, and at least one combination thereof.

27. The computer program product according to claim 23, wherein the lightweight representation is configured to minimize a number of lightweight characteristics used to generate the detailed representation of the at least one portion of the predetermined location;
the lightweight characteristics include at least one of the following: a polygon, a texture, a line, a photograph, and a graphical image;
the lightweight representation is configured to be stored in a memory coupled to the at least one programmable processor and configured to consume an amount of memory that is less than an amount of memory consumed by the spatial representation.

28. The computer program product according to claim 23, wherein the spatial representation of the predetermined location is a three-dimensional representation of the predetermined location.

29. The computer program product according to claim 23, wherein the operations further comprise
generating at least one new feature based on the at least one existing feature contained within the spatial representation of the predetermined location.

30. The computer program product according to claim 23, wherein at least one location point at the predetermined location is configured to define a relative positioning of at least one image of at least one portion at the predetermined location.

31. The computer program product according to claim 26, wherein the operations further comprise
obtaining at least one additional image of the at least one portion of the predetermined location; and
generating at least one user interface for allowing the user to edit at least one of the following: the first data for the predetermined location, the at least one distance measurement between at least two location points at the predetermined location, the at least one image of the at least one portion of the predetermined location, the at least one additional image of the at least one portion of the predetermined location, and at least one combination thereof.

32. The computer program product according to claim 31, wherein the operations further comprise
adding at least one drawing stroke to the merged first data for the predetermined location, the at least one distance measurement between at least two location points at the predetermined location, the at least one image of the at least one portion of the predetermined location, and the at least one additional image of the at least one portion of the predetermined location.

33. The computer program product according to claim 23, wherein the operations further comprise
correcting received first data using the at least one distance measurement between at least two location points at the predetermined location.

\* \* \* \* \*